United States Patent
Nishi et al.

(10) Patent No.: US 9,908,921 B2
(45) Date of Patent: Mar. 6, 2018

(54) MODIFIED GALECTIN-9 PROTEIN

(71) Applicant: NATIONAL UNIVERSITY CORPORATION KAGAWA UNIVERSITY, Takamatsu-shi, Kagawa (JP)

(72) Inventors: Nozomu Nishi, Kagawa (JP); Aiko Itoh, Kagawa (JP)

(73) Assignee: National University Corporation Kagawa University, Kagawa (JP)

( * ) Notice: Subject to any disclaimer, the term of this patent is extended or adjusted under 35 U.S.C. 154(b) by 14 days.

(21) Appl. No.: 14/443,558

(22) PCT Filed: Oct. 9, 2013

(86) PCT No.: PCT/JP2013/077514
§ 371 (c)(1),
(2) Date: May 18, 2015

(87) PCT Pub. No.: WO2014/080703
PCT Pub. Date: May 30, 2014

(65) Prior Publication Data
US 2015/0307574 A1 Oct. 29, 2015

(30) Foreign Application Priority Data
Nov. 20, 2012 (JP) ................. 2012-254349

(51) Int. Cl.
C07K 14/47 (2006.01)
A61K 38/00 (2006.01)

(52) U.S. Cl.
CPC .......... C07K 14/4726 (2013.01); A61K 38/00 (2013.01)

(58) Field of Classification Search
None
See application file for complete search history.

(56) References Cited

U.S. PATENT DOCUMENTS

| | | | |
|---|---|---|---|
| 8,268,324 B2 * | 9/2012 | Nishi | C07K 14/4726 424/192.1 |
| 8,580,743 B2 * | 11/2013 | Nishi | C07K 14/4726 424/192.1 |
| 2010/0203628 A1 | 8/2010 | Nishi et al. | |

FOREIGN PATENT DOCUMENTS

WO 2005/093064 10/2005

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Alignment to SEQ ID No. 2 of U.S. Pat. No. 8,268,324, Dec. 2016.*
Alignment to SEQ ID No. of U.S. Pat. No. 8,580,743, Dec. 2016.*
Singh et al. Curr Protein Pept Sci. 2017, 18, 1-11.*
Nishi et al., "Development of highly stable galectins: Truncation of the linker peptide confers protease-resistance on tandem-repeat type galectins", FEBS Letters, vol. 579, pp. 2058-2064 (2005).
Okudaira et al., "A modified version of galectin-9 suppresses cell growth and induces apotosis of humanT-cell leukemia virus type I-infected T-cell lines", Int. J. Cencer, vol. 120, pp. 2251-2261 (2007).
Yoshida et al., "X-ray structures of human galectin-9 C-terminal domain in complexes with a biantennary oligosaccharide and sialyl-lactose", J. Biol. Chem., vol. 285, No. 47, pp. 36969-36976 (2010).
Sato et al., "Functional analysis of the carbohydrate recognition domains and a linker peptide of galectin-9 as to eosinophil chemoattractant activity", Glycobiology, vol. 12, No. 3, pp. 191-197 (2002).
Türeci et al., "Molecular definition of a novel human galectin which is immunogenic in patients with Hodgkin's disease", J. Biol. Chem., vol. 272, No. 10, pp. 6416-6422 (1997).
Itoh et al., "Optimization of the inter-domain structure of galectin-9 for recombinant production",Glycobiology, vol. 23, No. 8, pp. 920-925 (2013).
International Search Report issued in International Application No. PCT/JP2013/077514, dated Nov. 19, 2013, 6 pages.

* cited by examiner

Primary Examiner — Christian Fronda
(74) Attorney, Agent, or Firm — Hamre, Schumann, Mueller & Larson, P.C.

(57) ABSTRACT

The present invention provides galectin-9 variant having substantially the same bioactivity as in wild-type galectin-9 and being superior in protease stability, solubility, and yield. The galectin-9 variant according to the present invention is a protein including the following NCRD and the following CCRD composed of an N-terminal region and a C-terminal region. The C terminus of the NCRD and the N terminus of the CCRD are directly or indirectly bound to each other. The NCRD is (N1) a peptide composed of an amino acid sequence represented by SEQ ID NO: 1. The N-terminal region of the CCRD is (C-N1) a peptide composed of an amino acid sequence obtained by deletion of 1 to 17 amino acids in an amino acid sequence represented by SEQ ID NO: 3. The C-terminal region is (C-C1) a peptide composed of an amino acid sequence represented by SEQ ID NO: 5.

13 Claims, 3 Drawing Sheets

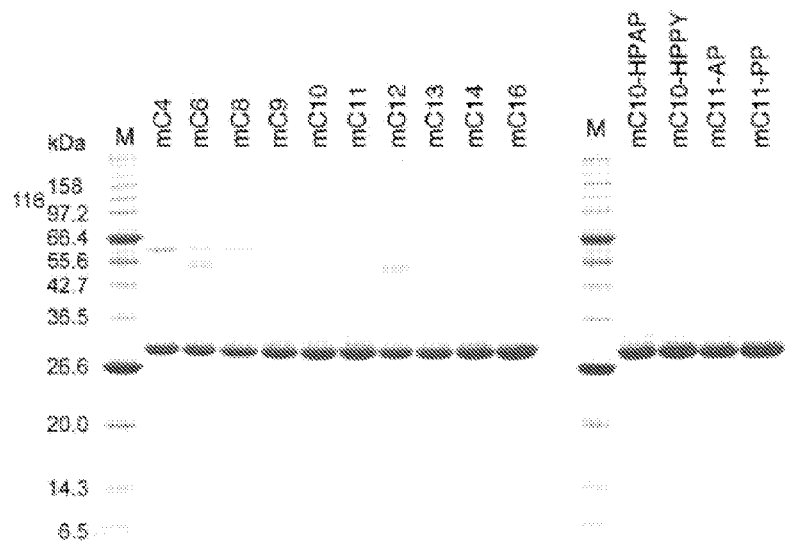

MODIFIED GALECTIN-9 PROTEIN

TECHNICAL FIELD

The present invention relates to galectin-9 protein variant.

BACKGROUND ART

The wild-type galectin-9 has a function of suppressing excess immunoreaction or repairing breakdown of immune system such as activation of immunity to cancer, through differentiation or homeostasis of T cells. The wild-type galectin-9 is composed of two Carbohydrate Recognition Domains (CRDs) and a link peptide region linking them. It is suggested that the wild-type galectin-9 that is a recombinant generated using *Escherichia coli* as a host induces suppression of transfer of cancer and regression of cancer by a direct action on tumor cells (activity of inducing adhesion among tumor cells and apoptosis of tumor cells) and an action via an immune system. Moreover, it is identified that the wild-type galectin-9 does not act on non-activated lymphocytes and induces activated T cells, specifically apoptosis of CD4-positive T cells which cause an excess immunoreaction. Furthermore, it is also identified that the wild-type galectin-9 has potent apoptosis inducibility to synoviocytes involved in such conditions as deformation of joints in rheumatism.

The above-mentioned functions of the wild-type galectin-9 show that the wild-type galectin-9 is useful as therapeutic drugs for various diseases. However, in order to actually distribute the wild-type galectin-9 as a therapeutic drug, there are three problems of protease sensitivity, low solubility, and low yield of recombinant protein. Regarding the problem of protease sensitivity of the wild-type galectin-9 among these problems, the inventors of the present invention have reported the stabilized galectin-9 having a molecular structure more stable to protease (Patent Document 1). However, no effective solution to the problems of low solubility and low yield of recombinant protein has been reported. Therefore, it is strongly required to provide galectin-9 variant superior in solubility and yield in order to commercialize a pharmaceutical utilizing superior functions of the wild-type galectin-9.

PRIOR ART DOCUMENTS

Patent Document

Patent Document 1: WO 2005/093064

SUMMARY OF INVENTION

Problem to be Solved by the Invention

Hence, the present invention is intended to provide a galectin-9 variant having a bioactivity that is substantially the same as wild-type galectin-9 and being superior in protease stability and solubility.

Means for Solving Problem

In order to achieve the aforementioned objects, the present invention is a protein or a salt thereof, including: NCRD; and CCRD, a C terminus of the NCRD and an N terminus of the CCRD being directly or indirectly bound to each other. The NCRD is (N1) a peptide composed of an amino acid sequence represented by SEQ ID NO: 1, (N2) a peptide which is composed of an amino acid sequence obtained by deletion, substitution, insertion and/or addition of one or more amino acids in the amino acid sequence represented by SEQ ID NO: 1 and has a carbohydrate binding ability, or (N3) a peptide which is composed of an amino acid sequence exhibiting an 80% or more identity to the amino acid sequence represented by SEQ ID NO: 1 and has a carbohydrate binding ability. The CCRD is a peptide composed of an N-terminal region and a C-terminal region and has a carbohydrate binding ability. The N-terminal region is (C-N1) a peptide composed of an amino acid sequence obtained by deletion of 1 to 17 amino acids in an amino acid sequence represented by SEQ ID NO: 3, and the C-terminal region is (C-C1) a peptide composed of an amino acid sequence represented by SEQ ID NO: 5, (C-C2) a peptide composed of an amino acid sequence obtained by deletion, substitution, insertion, and/or addition of one or more amino acids in the amino acid sequence represented by SEQ ID NO: 5, or (C-C3) a peptide composed of an amino acid sequence exhibiting an 80% or more identity to the amino acid sequence represented by SEQ ID NO: 5.

The nucleic acid according to the present invention includes a base sequence that encodes the protein according to the present invention.

The expression vector according to the present invention includes the nucleic acid according to the present invention.

The transformant according to the present invention includes the nucleic acid or the expression vector according to the present invention.

The pharmaceutical according to the present invention includes at least one of the protein or a salt thereof, the nucleic acid, and the expression vector according to the present invention.

The protein or a salt thereof according to the present invention is a wild-type galectin-9 variant and hereinafter referred to as the galectin-9 variant according to the present invention.

Effects of the Invention

The galectin-9 variant according to the present invention has the same bioactivity as wild-type galectin-9 and is superior in protease stability (also referred to as resistance or sensitivity) and solubility and is also superior in yield at the time of, for example, production as a recombinant protein due to the solubility. As described above, the galectin-9 variant according to the present invention not only has bioactivity of wild-type galectin, but also is superior in stability, handleability, and yield in production. Thus, it can be said that the galectin-9 variant according to the present invention is really useful as a pharmaceutical material.

BRIEF DESCRIPTION OF DRAWINGS

FIG. 1 is a schematic view showing a sequence of stabilized galectin-9.

FIG. 2 is a photograph showing a result of SDS-PAGE of the galectin-9 variant in Example 1 of the present invention.

DESCRIPTION OF EMBODIMENTS

1. Modified Galectin-9

Figure 3:
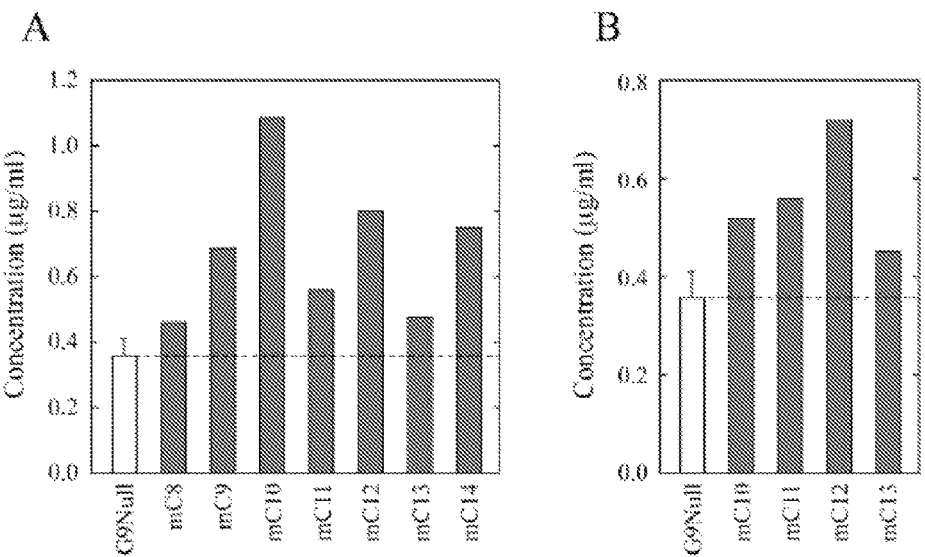
FIG. 3 shows graphs showing concentrations of the deletion-type galectin-9 variant in Example 1 of the present invention.

As mentioned above, the galectin-9 variant according to the present invention is a protein or a salt thereof, including: NCRD; and CCRD, a C terminus of the NCRD and an N terminus of the CCRD being directly or indirectly bound to each other. The NCRD is (N1) a peptide composed of an amino acid sequence represented by SEQ ID NO: 1, (N2) a peptide which is composed of an amino acid sequence obtained by deletion, substitution, insertion and/or addition of one or more amino acids in the amino acid sequence represented by SEQ ID NO: 1 and has a carbohydrate binding ability, or (N3) a peptide which is composed of an amino acid sequence exhibiting an 80% or more identity to the amino acid sequence represented by SEQ ID NO: 1 and has a carbohydrate binding ability. The CCRD is a peptide composed of an N-terminal region and a C-terminal region and has a carbohydrate binding ability. The N-terminal region is (C-N1) a peptide composed of an amino acid sequence obtained by deletion of 1 to 17 amino acids in an amino acid sequence represented by SEQ ID NO: 3, and the C-terminal region is (C-C1) a peptide composed of an amino acid sequence represented by SEQ ID NO: 5, (C-C2) a peptide composed of an amino acid sequence obtained by deletion, substitution, insertion, and/or addition of one or more amino acids in the amino acid sequence represented by SEQ ID NO: 5, or (C-C3) a peptide composed of an amino acid sequence exhibiting an 80% or more identity to the amino acid sequence represented by SEQ ID NO: 5.

The wild-type galectin-9 is a protein having two carbohydrate recognition domains (CRDs) as mentioned above. The galectin-9 variant according to the present invention has substantially the same bioactivity as wild-type galectin-9 and exhibits superior protease stability and solubility than the wild-type galectin-9. The galectin-9 variant according to the present invention further exhibits superior yield at that time of production as a recombinant protein due to the solubility, for example. In the present invention, "substantially the same bioactivity" means that the bioactivity of the galectin-9 variant is the same kind of bioactivity as or a similar kind of bioactivity to the wild-type galectin-9, for example. Examples of the bioactivity of the wild-type galectin-9 include binding activity specific to a specific carbohydrate strand, cytotoxic activity, apoptosis induction activity, anti-inflammatory activity, anti-allergy activity, immunomodulatory activity, physiological activity, and biological activity. In the present invention, the "substantially the same bioactivity as wild-type galection-9" means bioactivity associated with treatments of diseases and the like and does not encompass the meaning of protease stability, solubility, and yield that are the objects of the present invention, for example.

The galectin-9 variant according to the present invention preferably has bioactivity substantially the same or more than the wild-type galectin-9, for example. The "substantially the same bioactivity as wild-type galectin-9" means the same extent of the substantially the same bioactivity as wild-type galectin-9. The substantially the same or more than can be, for example, about 0.001 to about 100 times, preferably about 0.01 to about 100 times, more preferably about 0.1 to about 100 times, yet more preferably about 0.5 to about 100 times the bioactivity of the wild-type galectin-9.

In the present invention, the "solubility" means, for example, solubility to an aqueous medium, and examples of the aqueous medium include water, a saline solution, various buffer solutions such as a phosphate buffer solution and the like, and mixtures thereof.

In the galectin-9 variant according to the present invention, the NCRD is a C-type carbohydrate recognition domain (CRD) on the N terminus side, and the CCRD is a C-type carbohydrate recognition domain (CRD) on the C terminus side.

In the galectin-9 variant according to the present invention, the NCRD is, as mentioned above, any of the peptides (N1), (N2), and (N3). The NCRD is, as mentioned above, a peptide having a carbohydrate binding ability.

The peptide (N1) is composed of an amino acid sequence represented by SEQ ID NO: 1.

```
SEQ ID NO: 1: 148aa
MAFSGSQAPYLSPAVPFSGTIQGGLQDGLQITVNGTVLSSSGTRFAVNFQ

TGFSGNDIAFHFNPRFEDGGYVVCNTRQNGSWGPEERKTHMPFQKGMPFD

LCFLVQSSDFKVMVNGILFVQYFHRVPFHRVDTISVNGSVQLSYISFQ
```

The peptide (N2) is a peptide composed of an amino acid sequence obtained by deletion, substitution, insertion, and/or addition of one or more amino acids in the amino acid sequence of the peptide (N1). The peptide (N2) is only required to have the same function as the peptide (N1) and specifically have a carbohydrate binding ability and is not limited to particular peptides. One or more is, for example, 1 to 45, preferably 1 to 30, more preferably 1 to 15, yet more preferably 1 to 7, particularly preferably 1, 2, or 3.

The peptide (N3) is a peptide composed of an amino acid sequence exhibiting 70% or more identity to the amino acid sequence of the peptide (N1). The peptide (N3) is only required to have the same function as the peptide (N1) and specifically have a carbohydrate binding ability and is not limited to particular peptides. The identity is, for example, preferably 75% or more, more preferably 80% or more, yet more preferably 85% or more, yet more preferably 90% or more, particularly preferably 95% or more, 96% or more, 97% or more, 98% or more, 99% or more.

As mentioned above, the CCRD is a peptide composed an N-terminal region and a C-terminal region and has a carbohydrate binding ability. The N-terminal region and the C-terminal region are shown below and are only required to have a carbohydrate binding ability as the CCRD in the state of linking to each other.

The N-terminal region in the CCRD is the peptide (C-N1), i.e., a peptide composed of an amino acid sequence obtained by deletion of 1 to 17 amino acids in an amino acid sequence represented by SEQ ID NO: 3. The galectin-9 variant exhibiting the above-mentioned effects of the present invention is composed by the N-terminal region having such deletion of amino acids. Each of the 10th and 11th amino acids (X) in SEQ ID NO: 3 is proline or histidine, one of them is preferably proline, and XX is, for example, preferably Pro-Pro (PP), Pro-His (PH), or His-Pro (HP). Each of 12th and 13th amino acid residues (X) in SEQ ID NO: 3 is proline or alanine, one of them is preferably proline, and XX is, for example, preferably Pro-Pro (PP), Pro-Ala (PA), or Ala-Pro (AP).

```
SEQ ID NO: 3: 17aa
TPAIPPMMYXXXXYPMP
```

As to the number of amino acid residues to be deleted in the peptide (C-N1), the lower limit is 1, preferably 6, more preferably 8, the upper limit is 17, preferably 14, more preferably 13, yet more preferably 12, and the range is, for example, preferably 6 to 14, more preferably 8 to 14 or 9 to 14, yet more preferably 8 to 13 or 9 to 13, particularly preferably 10 to 12. In the present invention, the description of the numerical range means the disclosure of values included in the range. That is, for example, the description of 6 to 14 means the disclosure of 6, 7, 8, 9, 10, 11, 12, 13, and 14.

The deletion of amino acids in the peptide (C-N1) may be any of the deletion of consecutive amino acids and the deletion of non-consecutive amino acids, for example. The deletion is preferably the deletion of consecutive amino acids, particularly preferably the deletion of consecutive amino acid from the N terminus. Both of the deletion of consecutive amino acids and the deletion of non-consecutive amino acids may be present in the N terminal region. As the deletion of consecutive amino acids, the above-mentioned number of amino acids is preferably deleted, and as a specific example, for example, preferably 6 to 14 amino acids, more preferably 8 to 14 amino acids or 9 to 14 amino acids, yet more preferably 8 to 13 amino acids or 9 to 13 amino acids, particularly preferably 10 to 12 amino acids are deleted based on the amino acid at the N terminus as a first amino acid.

It is preferred that a proline residue is conserved in the peptide (C-N1). Specifically, it is preferred that, in the amino acid sequence represented by SEQ ID NO: 3, at least one amino acid residue selected from the group consisting of 10th, 11th, 12th, 13th, 15th, and 17th amino acid residues is proline Moreover, as mentioned above, it is preferred that, in the amino acid sequence represented by SEQ ID NO: 3, at least one of the 10th and the 11th amino acid residues is proline, and they are, for example, Pro-Pro (PP), Pro-His (PH), or His-Pro (HP). As mentioned above, it is preferred that, in the amino acid sequence represented by SEQ ID NO: 3, at least one of the 12th and the 13th amino acid residues is proline, and they are, for example, Pro-Pro (PP), Pro-Ala (PA), or Ala-Pro (AP).

Specific examples of the peptide (C-N1) include amino acid sequences represented by SEQ ID NOs: 7 to 20. In the present invention, the peptide (C-N1) is not limited to the following amino acid sequences.

TABLE 1

| | N-terminal region in CCRD | |
|---|---|---|
| | Amino acid sequence | SEQ ID NO |
| mC8 | YPHPAYPMP | 7 |
| mC9 | PHPAYPMP | 8 |
| mC9-HP | HPPAYPMP | 9 |

TABLE 1-continued

| | N-terminal region in CCRD | |
|---|---|---|
| | Amino acid sequence | SEQ ID NO |
| mC10 | HPAYPMP | 10 |
| mC10-1P1A1 | HAAYPMP | 11 |
| mC10-1P1A2 | HPAYAMP | 12 |
| mC10-HPAP | HPAPPMP | 13 |
| mC10-HPPY | HPPYPMP | 14 |
| mC11 | PAYPMP | 15 |
| mC11-AP | APYPMP | 16 |
| mC11-PP | PPYPMP | 17 |
| mC12 | AYPMP | 18 |
| mC13 | YPMP | 19 |
| mC14 | PMP | 20 |

The peptide of the C-terminal region in the CCRD is, as mentioned above, any of the peptides (C-C1), (C-C2), and (C-C3).

The peptide (C-C1) is composed of an amino acid sequence represented by SEQ ID NO: 5.

SEQ ID NO: 5: 129aa
FITTILGGLYPSKSILLSGTVLPSAQRFHINLCSGNHIAFHLNPRFDENA

VVRNTQIDNSWGSEERSLPRKMPFVRGQSFSVWILCEAHCLKVAVDGQHL

FEYYHRLRNLPTINRLEVGGDIQLTHVQT

The peptide (C-C2) is composed of an amino acid sequence obtained by deletion, substitution, insertion, and/or addition of one or more amino acids in the amino acid sequence of the peptide (C-C1). One or more is, for example, 1 to 39, preferably 1 to 26, more preferably 1 to 13, yet more preferably 1 to 6, particularly preferably 1, 2, or 3.

The peptide (C-C3) is composed of an amino acid sequence exhibiting 70% or more identity to the amino acid sequence in the peptide (C-C1). The identity is, for example, preferably 75% or more, more preferably 80% or more, yet more preferably 85% or more, yet more preferably 90% or more, particularly preferably, 95% or more, 96% or more, 97% or more, 98% or more, 99% or more.

Specific examples of the CCRD composed of the N-terminal region and the C-terminal region include amino acid sequences represented by SEQ ID NOs: 21 to 34. In the present invention, the peptide of the CCDR is not limited to the following sequences.

TABLE 2

| | CCRD | | |
|---|---|---|---|
| | Sequence | Amino acid SEQ ID NO | Base SEQ ID NO |
| mC8 | YPHPAYPMPFITTILGGLYPSKSILLSGTVLPSAQRFHINLCSGNHI AFHLNPRFDENAVVRNTQIDNSWGSEERSLPRKMPFVRGQSFSVWIL CEAHCLKVAVDGQHLFEYYHRLRNLPTINRLEVGGDIQLTHVQT | 21 | 63 |

TABLE 2-continued

CCRD

| | Sequence | Amino acid SEQ ID NO | Base SEQ ID NO |
|---|---|---|---|
| mC9 | PHPAYPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 22 | 64 |
| mC9-HP | HPPAYPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 23 | 65 |
| mC10 | HPAYPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 24 | 66 |
| mC10-1P1A1 | HAAYPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 25 | 67 |
| mC10-1P1A2 | HPAYAMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 26 | 68 |
| mC10-HPAP | HPAPPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 27 | 69 |
| mC10-HPPY | HPPYPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 28 | 70 |
| mC11 | PAYPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 29 | 71 |
| mC11-AP | APYPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 30 | 72 |
| mC11-PP | PPYPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 31 | 73 |
| mC12 | AYPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 32 | 74 |
| mC13 | YPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 33 | 75 |
| mC14 | PMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQHLFEYYHRLRNLPTINRLEVGGDIQLTHVQT | 34 | 76 |

In the galectin-9 variant according to the present invention, the NCRD and the CCRD may be, as mentioned above, proteins which are directly or indirectly bound to each other and are preferably the former.

In the latter case, the C terminus of the NCRD and the N terminus of the CCRD may be indirectly bound to each other via a linker, for example. Examples of the linker include an amino acid and a peptide. The number of amino acid residues in the peptide is not limited to particular numbers, preferably is low, and is, for example, 2 to 5, preferably 4 or less, 3 or less, 2 or less, 1.

The sequence of the peptide is not limited to particular sequences and can be set appropriately. Specific examples of the peptide includes peptides including or composed of sequences such as His-Met (HM), Arg-Ile-Pro (RIP), Asn-Leu (NL), Asp-Phe-Val (DFV), and Gly-Ser-Ala (GSA).

A specific example of the galectin-9 variant according to the present invention can be a peptide composed of any one of amino acid sequences of SEQ ID NOs: 35 to 48 shown in Table 3. The galectin-9 variant according to the present invention is not limited to these examples.

TABLE 3

| | Full length | |
|---|---|---|
| | Amino acid SEQ ID NO | Base SEQ ID NO |
| mC8 | 35 | 77 |
| mC9 | 36 | 78 |
| mC9-HP | 37 | 79 |
| mC10 | 38 | 80 |
| mC10-1P1A1 | 39 | 81 |
| mC10-1P1A2 | 40 | 82 |
| mC10-HPAP | 41 | 83 |
| mC10-HPPY | 42 | 84 |
| mC11 | 43 | 85 |

TABLE 3-continued

| | Full length | |
|---|---|---|
| | Amino acid SEQ ID NO | Base SEQ ID NO |
| mC11-AP | 44 | 86 |
| mC11-PP | 45 | 87 |
| mC12 | 46 | 88 |
| mC13 | 47 | 89 |
| mC14 | 48 | 90 |

In the amino acid sequence of the galectin-9 variant according to the present invention, each of the amino acids may be substituted with another amino acid or amino acid analogue in the class to which the each amino acid belongs, for example. The class can be, for example, a class defined by chemical characteristics and/or physical characteristics. Examples of the characteristics includes hydrophobicity, hydrophilicity, electric charge, and size, and specific examples thereof include non-polar amino acid (hydrophobic amino acid), polar amino acid (neutral amino acid), positive charge amino acid (acidic amino acid), and negative charge amino acid (acidic amino acid). Examples of the non-polar amino acid include alanine, phenylalanine, leucine, isoleucine, valine, proline, tryptophan, and methionine. Examples of the polar amino acid include glycine, serine, threonine, cysteine, tyrosine, asparagine, and glutamine. Examples of the positive charge amino acid include arginine, lysine, and histidine. Examples of the negative charge amino acid include aspartic acid and glutamic acid.

In the galectin-9 variant according to the present invention, the salt of the protein is not limited to particular salts and may be in the form of a salt of any of the above-mentioned proteins.

The galectin-9 variant according to the present invention is only required to exert the effects of the present invention, and an amino acid residue(s) may be further varied, for example. Examples of the variation include partial dissociation of amino acid residues, variation to a derivative, binding of a protecting group, and binding of a carbohydrate strand, and specific examples thereof include amidation and esterification of a carboxyl group such as the C terminus.

A method for producing the galectin-9 variant according to the present invention is not limited to particular methods, and the galectin-9 variant may be produced by gene-engineering techniques or synthesis techniques, based on the amino acid sequence, for example. The former may be a cell system using a host or an acellular protein synthesis system, for example. In the case of the gene-engineering techniques, for example, a nucleic acid having a base sequence corresponding to the amino acid sequence, an expression vector including the nucleic acid, and the like can be used. The method for producing the galectin-9 variant, the nucleic acid which encodes the galectin-9 variant, and the expression vector are described below.

2. Nucleic Acid, Expression Vector, and Transformant
(1) Nucleic Acid

The nucleic acid according to the present invention includes a base sequence which encodes the galectin-9 variant according to the present invention. A protein which encodes the nucleic acid is caused to express in a host or an acellular protein synthesis system by gene-engineering techniques using the nucleic acid according to the present invention, for example. Thus, the galectin-9 variant according to the present invention can be produced.

The base sequence of the nucleic acid according to the present invention is not limited to particular base sequences and can be designed by replacement with a codon based on the amino acid sequence of the galectin-9 variant according to the present invention. The nucleic acid according to the present invention can be synthesized by gene-engineering techniques or organic synthesis techniques and can be referred to as synthesized DNA such as cDNA or synthesized RNA. The nucleic acid according to the present invention may be, for example, any of a sense strand and an antisense strand and may be a hybrid thereof.

The nucleic acid according to the present invention can be, for example, a polynucleotide including a polynucleotide that encodes the NCRD (NCRD polynucleotide) and a polynucleotide that encodes the CCRD (CCRD polynucleotide), wherein the 5' end of the CCRD polynucleotide is directly or indirectly bound to the 3' end of the NCRD polynucleotide. A reading frame of the NCRD polynucleotide and a reading frame of the CCRD polynucleotide are bound to each other so as to correspond to the amino acid of the NCRD and the amino acid of the CCRD, for example. In the case of the indirect binding, a linker may be present between the NCRD polynucleotide and the CCRD polynucleotide. In this case, it is preferred that the sequence of the linker is designed so that the reading frame of the CCRD polynucleotide does not change. The linker is, for example, a polynucleotide.

In the NCRD, the polynucleotide (n1) that encodes the peptide (N1) is represented by a base sequence represented by SEQ ID NO: 2, for example.

SEQ ID NO: 2
atggccttcagcggttcccaggctccctacctgagtccagctgtcccctt ttctgggactattcaaggaggtctccaggacggacttcagatcactgtca atgggaccgttctcagctccagtggaaccaggttttgctgtgaactttcag actggcttcagtggaaatgacattgccttccacttcaaccctcggtttga agatggagggtacgtggtgtgcaacacgaggcagaacggaagctgggggc ccgaggagaggaagacacacatgcctttccagaaggggatgccctttgac ctctgcttcctggtgcagagctcagatttcaaggtgatggtgaacggtat cctcttcgtgcagtacttccaccgcgtgcccttccaccgtgtggacacca tctccgtcaatggctctgtgcagctgtcctacatcagcttccag The polynucleotide (c-n1) that encodes the peptide (C-N1) that is the N-terminal region of the CCRD is, for example, represented by a base sequence obtained by deletion of 1 to 17 sets of codon consisting of three consecutive bases as one set in a base sequence represented by SEQ ID NO: 4. The number of sets of codon to be deleted and the position(s) of the codon(s) to be deleted correspond to the number of amino acid residues to be deleted and the position(s) of the amino acid(s) to be deleted described for the peptide (C-N1), for example. In SEQ ID NO: 4, the underlined bases represent a sequence that encodes the 10th to 13th (four) amino acids in SEQ ID NO: 3 and can be set appropriately depending on the amino acids.

SEQ ID NO: 4
actcccgccatcccacctatgatgta<u>cnnnnnnnnnnnnn</u>tatccgatgc ct

Specific examples of the polynucleotide (c-n1) include the following base sequences, for example. In the present invention, the polynucleotide (c-n1) is not limited to the following sequences.

TABLE 4

N-terminal region in CCRD

| | Base sequence | SEQ ID NO |
|---|---|---|
| mC8 | tacccccaccccgcctatccgatgcct | 49 |
| mC9 | ccccacccegcctatccgatgcct | 50 |
| mC9-HP | cacccgcccgcctatccgatgcct | 51 |
| mC10 | cacccegcctatccgatgcct | 52 |
| mC10-1P1A1 | cacgccgcctatccgatgcct | 53 |
| mC10-1P1A2 | cacccegcctatgcgatgcct | 54 |
| mC10-HPAP | cacccegccccgccgatgcct | 55 |
| mC10-HPPY | cacccccectatccgatgcct | 56 |
| mC11 | cccgcctatccgatgcct | 57 |
| mC11-AP | gccccctatccgatgcct | 58 |
| mC11-PP | cccccctatccgatgcct | 59 |
| mC12 | gcctatccgatgcct | 60 |
| mC13 | tatccgatgcct | 61 |
| mC14 | ccgatgcct | 62 |

In the C-terminal region of the CCRD, the polynucleotide (c-c1) that encodes the peptide (C-C1) is, for example, represented by the base sequence of SEQ ID NO: 6.

SEQ ID NO: 6
ttcatcaccaccattctgggagggctgtacccatccaagtccatcctcct gtcaggcactgtcctgcccagtgctcagaggttccacatcaacctgtgct ctgggaaccacatcgccttccacctgaaccccegttttgatgagaatgct gtggtccgcaacacccagatcgacaactcctgggggtctgaggagcgaag tctgccccgaaaaatgcccttcgtccgtggccagagettctcagtgtgga tcttgtgtgaagctcactgcctcaaggtggccgtggatggtcagcacctg tttgaatactaccatcgcctgaggaacctgcccaccatcaacagactgga agtgggggcgacatccagctgacccatgtgcagacatag A specific example of the polynucleotide that encodes the CCRD (CCRD polynucleotide) composed of the N-terminal region and the C-terminal region can be a base sequence in which the 5' end of the base sequence represented by SEQ ID NO: 6 is linked to the 3' end of any of the base sequences represented by the sequence numbers shown in Table 2 (SEQ ID NOs: 63 to 76 shown in Table 2). In the present invention, the CCRD polynucleotide is not limited to these sequences.

A specific example of the nucleic acid that encodes the galectin-9 variant according to the present invention can be a polynucleotide composed of any of base sequences represented by SEQ ID NOs: 77 to 90 shown in Table 3. The nucleic acid according to the present invention is not limited to these examples.

In the nucleic acid, the polynucleotide may be DNA or RNA, for example. RNA can be, for example, a base sequence obtained by substitution of T in the base sequence of DNA shown as an example with U. DNA can be, for example, a sequence including or composed of deoxyribonucleotide, and RNA can be, for example, a sequence including or being composed of ribonucleotide. Moreover, the nucleic acid may be, for example, a sequence composed of artificial nucleic acids or a sequence in which the DNA or RNA further includes artificial nucleic acids. Examples of the artificial nucleic acids include LNA, PNA, and BNA.

(2) Expression Vector

The expression vector according to the present invention includes the nucleic acid according to the present invention. The expression vector according to the present invention is introduced into a host, and the protein that encodes the nucleic acid is expressed by the resultant transformant, for example. Thus, the galectin-9 variant according to the present invention can be produced. The expression vector according to the present invention is only required to functionally include the nucleic acid according to the present invention so that the galectin-9 variant according to the present invention can be expressed, and the other configuration is not limited to particular configurations.

The expression vector is only required to express the galectin-9 variant according to the present invention by introducing into a non-human host, for example. The non-human host is not limited to particular hosts and can be selected appropriately. Examples of the non-human host include microorganisms, animal cells, insect cells, plant cells, and cultured cells thereof. Examples of the microorganisms include prokaryotes and eukaryotes. Examples of the prokaryotes include bacteria belonging to *Escherichia* such as *Escherichia coli*, bacteria belonging to *Bacillus* such as *Bacillus subtilis*, bacteria belonging to *Pseudomonas* such as *Pseudomonas putida*, and bacteria belonging to *Rhizobium* such as *Rhizobium* Examples of the eukaryote include yeast such as *Saccharomyces cerevisiae* and *Schizosaccharomyces pombe*. Examples of the animal cells include COS cells and CHO cells. Examples of the insect cells include Sf9 cells and Sf21 cells.

The expression vector can be produced by inserting the nucleic acid into a vector which becomes a skeleton (hereinafter also referred to as a "basic vector"), for example. The kind of the basic vector is not limited to particular kinds and can be determined appropriately depending on the kind of the host into which the expression vector is introduced, for example. In the case where bacteria such as *Escherichia coli* are transformed, examples of the basic vector include a pET vector (Merck), a pCold vector (TAKARA BIO INC.), and a PQE vector (QIAGEN). In the case where eukaryotes such as yeast are transformed, the basic vector can be, for example, pYE22m, and a commercially available vector for yeast expression such as pYES (Invitrogen) or pESC (Stratagene) can also be used. In the case where the transformation is performed using an *Agrobacterium* method, the basic vector is, for example, preferably a binary vector, and examples thereof include pBI121, pPZP202, pBINPLUS, and pBIN19.

The expression vector preferably includes a regulatory sequence which regulates expression of nucleic acid and protein, for example. Examples of the regulatory sequence include a promoter, a terminator, an enhancer, a polyadenylation signal sequence, and an ori sequence (ori). The derivation of the promoter is not limited to particular derivations, and examples thereof include cytomegalovirus (CMV), Rous sarcoma virus (RSV), simian virus-40 (SV- 40), a muscle β actin promoter, and herpes simplex virus. Examples of the promoter further includes, besides these, a tissue-specific promoter such as a thymidine kinase promoter, a regulatory promoter such as a growth hormone regulatory promoter, a promoter under control of lac operon sequence, and an inducible promoter such as a zinc inducible metallothionein promoter. In the expression vector, the arrangement of the regulatory sequence is not limited to particular arrangements. In the expression vector, for example, the regulatory sequence is only required to be arranged so that the expression of nucleic acid and protein can be functionally regulated and can be arranged based on a known method. As the regulatory sequence, for example, a sequence including a basic vector in advance may be utilized, or the regulatory sequence may be further inserted into the basic vector. The regulatory sequence including the basic vector may be replaced with another regulatory sequence.

The expression vector may further have a coding sequence of a selection marker, for example. Examples of the selection marker include a drug resistance marker, a fluorescent protein marker, an enzyme marker, and a cell surface receptor marker.

(3) Transformant

The transformant according to the present invention includes the nucleic acid according to the present invention or the expression vector according to the present invention. The transformant according to the present invention is only required to functionally include the nucleic acid according to the present invention so that the galectin-9 variant according to the present invention can be expressed, and the other configurations are not limited to particular configurations.

The transformant can be obtained by introducing the nucleic acid according to the present invention into a host, for example. The host is not limited to particular hosts, and examples thereof include the above-mentioned non-human hosts. The transformant according to the present invention may include the nucleic acid according to the present invention as the expression vector according to the present invention, for example, and in this case, the transformant can be obtained by introducing the expression vector according to the present invention into a host, for example.

The method for introducing the nucleic acid or the expression vector into a host is not limited to particular methods, and the introduction can be performed by a known method. The method for the introduction can be set appropriately depending on the kind of the host.

The method for the introduction includes an introduction method using a gene gun such as a particle gun, a calcium phosphate method, a polyethyleneglycol method, a lipofection method using liposome, an electroporation method, an ultrasound nucleic acid introduction method, a DEAE-dextran method, a direct injection method using a micro glass tube, a hydrodynamic method, a cationic liposome method, a method using an introduction adjuvant, and a method via *Agrobacterium*. Examples of the lipsome include lipofectamine and cationic liposome. Examples of the introduction adjuvant include atelocollagen, nanoparticles, and a polymer.

3. Method for Producing Galectin-9 Variant

The method for producing the galectin-9 variant according to the present invention (hereinafter also referred to as "the production method according to the present invention") includes the step of expressing the nucleic acid according to the present invention, for example. The production method according to the present invention allows the galectin-9 variant to be obtained with a superior yield compared with the case of producing a wild-type galectin-9 as a recombinant protein, for example.

The production method according to the present invention is characterized in that the nucleic acid according to the present invention is transcribed and translated to a protein that is encoded by the nucleic acid by the expression of the nucleic acid to synthesize the galectin-9 variant according to the present invention, and the other steps and conditions are not limited to particular steps and conditions.

In the production method according to the present invention, the expression of the nucleic acid according to the present invention may be, for example, as mentioned above, performed in a cell system using a host or an acellular protein synthesis system.

In the case of a cell system, for example, the galectin-9 variant according to the present invention can be synthesized by introducing the nucleic acid according to the present invention into a host. The host is, for example, as mentioned above, and the introduction of the nucleic acid according to the present invention into a host may be an introduction of the expression vector according to the present invention.

The production method according to the present invention preferably further include the step of cultivating a transformant obtained by the introduction of the nucleic acid according to the present invention into a host. The conditions of the step of cultivating are not limited to particular conditions and can be determined appropriately depending on the kind of the host.

The expressed galectin-9 variant according to the present invention may be used as it is after the expression or may be used after purification, for example. The method for the purification is not limited to particular methods, and examples thereof include salting out, electrophoresis, and various kinds of chromatography.

4. Uses of Galectin-9 Variant

The galectin-9 variant according to the present invention can be used as a pharmaceutical. Specifically, the galectin-9 variant conserves, for example, activity of wild-type galectin 9, such as, e.g., cytotoxic activity against malignant tumors, apoptosis induction activity against malignant tumors, anti-tumor activity against malignant tumors, apoptosis induction activity against activated T cells (e.g., CD4-positive T cells) or activated B cells, immunomodulatory activity, anti-inflammatory activity, and/or anti-allergy activity. Thus, the galectin-9 variant according to the present invention is applicable to the same pharmaceuticals as those to which the wild-type galectin 9 is applicable, for example.

That is, the pharmaceutical according to the present invention contains at least one of the galectin-9 variant (a protein or a salt thereof) according to the present invention, the nucleic acid according to the present invention, and the expression vector according to the present invention, and is characterized in that it is applicable to at least one use selected from the group consisting of immunomodulatory agents (which also encompass immunosuppressive agents), anti-tumor agents, tumor metastasis inhibitors, analgesic agents, anti-inflammatory agents, and antiphlogistics. When the pharmaceutical according to the present invention contains the nucleic acid according to the present invention or the expression vector according to the present invention, it is only required that, for example, the galectin-9 variant according to the present invention can be expressed by the nucleic acid in the body of a patient to which the pharmaceutical according to the present invention has been administered.

The pharmaceutical according to the present invention can be used for treatment or prevention of diseases, for example. The treatment may be either causal treatment or symptomatic treatment. Also, the treatment may be any of disappearance of symptoms, alleviation (improvement) of symptoms, and inhibition of the progression of symptoms, for example.

A subject to which the pharmaceutical according to the present invention is administered is not limited to particular subjects, and examples thereof include humans and non-human animals excluding humans. Examples of the non-human animals include mammals such as mice, rats, rabbits, horses, sheep, cows, pigs, dogs, and cats; fishes; birds such as chickens; helminths; insects; reptiles; and amphibians.

The administration method of the pharmaceutical according to the present invention is not limited to particular methods and can be determined appropriately depending on the type of disease. The administration method may be, for example, either oral administration or parenteral administration, and also, may be either direct administration or indirect administration. Examples of the parenteral administration include local, transdermal, intravenous, intramuscular, subcutaneous, intradermal, and intraperitoneal administrations.

When the pharmaceutical according to the present invention contains the galectin-9 variant according to the present invention, the dose of the pharmaceutical is not limited to particular doses and can be determined appropriately depending on a subject to which the pharmaceutical is administered, the type of disease, the severity of the disease, etc. A specific example is as follows: the daily dose per a kilogram body weight of a subject is, for example, 5 µg to 5 mg, preferably 50 µg to 500 µg, more preferably 100 µg to 500 µg, and yet more preferably 200 µg to 250 µg. The frequency of administration per day is, for example, 1 to 3 times.

When the pharmaceutical according to the present invention contains the nucleic acid according to the present invention, the administration method thereof may be either in vivo administration or ex vivo administration, for example. In the former case, the administration may be achieved by, for example, administering the nucleic acid according to the present invention to the living body of a patient. In the latter case, the administration may be achieved by, for example, transfecting an isolated tissue or isolated cells with the nucleic acid according to the present invention and then introducing the tissue or cells to the living organism of a patient.

When the pharmaceutical according to the present invention contains the nucleic acid according to the present invention, the dose of the pharmaceutical is not limited to particular doses and can be determined appropriately depending on a subject to which the pharmaceutical is administered, the type of disease, the severity of the disease, etc. The dose preferably is such that, for example, it allows the galectin-9 variant according to the present invention in the above-described amount to be expressed. A specific example is as follows: when the nucleic acid is administered locally, the daily dose per human tissue is, for example, 100 ng to 200 mg, preferably 500 ng to 50 mg, more preferably 1 µg to 2 mg, and still more preferably 5 µg to 500 µg. The frequency of administration per day is, for example, 1 to 3 times.

The form of the pharmaceutical according to the present invention can be determined appropriately depending on the administration method, examples of which are as described above, for example. Examples of the form of the pharmaceutical include solution formulations, dispersion formulations, semisolid formulations, powder and granular formulations, molded formulations, and extract formulations. Specific examples thereof include tablets, coated tablets, sugar-coated tablets, pills, troches, hard capsules, soft capsules, microcapsules, implants, powders, micro powders, granules, microgranules, injections, pharmaceutical solutions, elixirs, emulsions, irrigations, syrups, liquid medicines, emulsions, suspensions, liniments, lotions, aerosols, sprays, inhalants, liquid medicines for use in atomizers, ointment formulations, plaster formulations, patches, pastes, cataplasms, creams, oil-based medicines, suppositories (e.g., rectal suppositories), tinctures, liquid medicines for skin, eye drops, nasal drops, ear drops, embrocations, infusions, pharmaceutical solutions for injections, powders for use in preparation of liquid formulations, freeze-dried formulations, and gel preparations.

The pharmaceutical according to the present invention may contain a pharmaceutically acceptable additive(s), in addition to the galectin-9 variant according to the present invention, the nucleic acid according to the present invention, or the expression vector according to the present invention. The additive is not limited to particular additives, and can be selected appropriately depending on the form of the pharmaceutical. Any known substances for use in preparation of pharmaceuticals can be used as the additive. The amount of the additive contained in the pharmaceutical is only required to not interfere with the properties of the galectin-9 variant according to the present invention contained in the pharmaceutical as an active ingredient and is not limited to particular amounts. Examples of the additive include carriers, adjuvants, excipients, bulking agents, diluents, flavoring agents, fragrances, sweetening agents, vehicles, antiseptic agents, stabilizers, binding agents, pH adjusters, buffers, surfactants, bases, solvents, fillers, expanders, dissolution assisting agents, solubilizers, tonicity agents, emulsifying agents, suspending agents, dispersants, thickening agents, gelling agents, curing agents, absorbents, adhesives, elastic agents, plasticizers, disintegrants, propellants, preservatives, antioxidants, sunproofing agents, moisturizing agents, palliatives, antistatic agents, and soothing agents. One kind of additive may be used, or two or more kinds of additives may be used in combination.

EXAMPLES

The present invention will be described in detail with reference to examples below. However, the present invention is not limited to the aspects described in the examples.

Example 1

As mentioned above, the stabilized galectin-9 composed of the amino acid sequence obtained by deletion of the region from proline at position 149 to serine at position 177 in wild-type galectin-9M has been reported in WO 2005/093064. The amino acid sequence of the stabilized galectin-9 is shown in FIG. 1 (SEQ ID NO: 91). It has been demonstrated that the stabilized galectin-9 maintains the bioactivity of wild-type galectin-9M and has superior protease stability than the wild-type galectin-9M. Hence, the solubility, bioactivity, and protease stability of galectin-9 variants obtained by varying the stabilized galectin-9 were examined.

(1) Construction of Expression Vector
(1-1) Deletion Type Galectin-9 Variant

As galectin-9 variants, proteins each composed of the amino acid sequence in which NCRD and CCRD are directly linked were used. Among the variants, the amino acid sequence (SEQ ID NO: 1) of the NCRD and the amino acid sequence (SEQ ID NO: 5) of the C-terminal region of the CCRD were common, and only the N-terminal region of the CCRD was set to an amino acid sequence obtained by deletion of 4, 6, 8, 9, 10, 11, 12, 13, 14, or 16 amino acid residue from the N-terminus in the amino acid sequence (17 amino acid residues) of SEQ ID NO: 3. The respective galectin-9 variants are referred to as galectin-9 variants mC4, mC6, mC8, mC9, mC10, mC11, mC12, mC13, mC14, and mC16 according to the number of amino acids deleted in the N-terminal region of the CCRD. The amino acid sequences and the base sequences of the N-terminal region of the CCRD of and the full-length amino acid sequences and the full-length base sequences of the stabilized galectin-9 and the galectin-9 variants are summarized below.

TABLE 5

| | | N-terminal region in CCRD | | Full-length | |
|---|---|---|---|---|---|
| | Amino acid sequence | Amino acid SEQ ID NO | Base SEQ ID NO | Amino acid SEQ ID NO | Base SEQ ID NO |
| G9Null | TPAIPPMMYXXXXYPMP (XXXX = PHPA) | 3 | 4 *1 | 91 | 92 |
| mC8 | YPHPAYPMP | 7 | 49 | 35 | 77 |
| mC9 | PHPAYPMP | 8 | 50 | 36 | 78 |
| mC10 | HPAYPMP | 10 | 52 | 38 | 80 |
| mC11 | PAYPMP | 15 | 57 | 43 | 85 |
| mC12 | AYPMP | 18 | 60 | 46 | 88 |
| mC13 | YPMP | 19 | 61 | 47 | 89 |
| mC14 | PMP | 20 | 62 | 48 | 90 |

*1 In SEQ ID NO: 4, consecutive twelve bases are ccccacccccgcc (SEQ ID NO: 130) which encodes PHPA (SEQ ID NO: 132).

The expression vectors that express the galectin-9 variants were constructed by the following method. The amino acid sequence (SEQ ID NO: 91) of the stabilized galectin-9 (hereinafter, also referred to as G9Null) in Example 1 of WO 2005/093064 is shown in FIG. 1. First, the coding sequence (SEQ ID NO: 92) for the G9Null was inserted into the cloning site (BamHI site) of pET-11a, and an expression vector pET-G9Null of the G9Null was constructed in the usual manner. It has been already verified in WO 2005/093064 that the stabilized galectin-9 has the apoptosis induction activity of wild-type galectin-9 and has superior protease stability than the wild-type galectin-9.

SEQ ID NO: 92
ATGGCCTTCAGCGGTTCCCAGGCTCCCTACCTGAGTCCAGCTGTCCCCTT

TTCTGGGACTATTCAAGGAGGTCTCCAGGACGGACTTCAGATCACTGTCA

ATGGGACCGTTCTCAGCTCCAGTGGAACCAGGTTTGCTGTGAACTTTCAG

ACTGGCTTCAGTGGAAATGACATTGCCTTCCACTTCAACCCTCGGTTTGA

AGATGGAGGGTACGTGGTGTGCAACACGAGGCAGAACGGAAGCTGGGGGC

CCGAGGAGAGGAAGACACACATGCCTTTCCAGAAGGGGATGCCCTTTGAC

CTCTGCTTCCTGGTGCAGAGCTCAGATTTCAAGGTGATGGTGAACGGTAT

CCTCTTCGTGCAGTACTTCCACCGCGTGCCCTTCCACCGTGTGGACACCA

TCTCCGTCAATGGCTCTGTGCAGCTGTCCTACATCAGCTTCCAGCATATG

ACTCCCGCCATCCCACCTATGATGTACCCCCACCCCGCCTATCCGATGCC

TTTCATCACCACCATTCTGGGAGGGCTGTACCCATCCAAGTCCATCCTCC

TGTCAGGCACTGTCCTGCCCAGTGCTCAGAGGTTCCACATCAACCTGTGC

TCTGGGAACCACATCGCCTTCCACCTGAACCCCCGTTTTGATGAGAATGC

TGTGGTCCGCAACACCCAGATCGACAACTCCTGGGGGTCTGAGGAGCGAA

GTCTGCCCCGAAAAATGCCCTTCGTCCGTGGCCAGAGCTTCTCAGTGTGG

ATCTTGTGTGAAGCTCACTGCCTCAAGGTGGCCGTGGATGGTCAGCACCT

GTTTGAATACTACCATCGCCTGAGGAACCTGCCCCACCATCAACAGACTGG

AAGTGGGGGCGACATCCAGCTGACCCATGTGCAGACATAG

NCRD polynucleotide (SEQ ID NO: 2) which encodes NCRD peptide (SEQ ID NO: 1) was amplified by PCR using the following primers A1 and A2 with the pET-G9Null being used as a target sequence and purified by agarose gel electrophoresis.

(Primer)
A1:
(SEQ ID NO: 93)
5'-CGTCCTCGTCCTCATATGGCCTTCAGCGGTTCCCAGGCT-3'

A2:
(SEQ ID NO: 94)
5'-CTGGAAGCTGATGTAGGACAGCTG-3'

In the same manner, polynucleotides (CCRD1 to CCRD10, 10 types) which encode CCRDs of the respective variants were amplified by PCR using the following primer A4 and the following primers B1 to K1 corresponding to the respective variants with the pET-G9Null being used as a target sequence and purified by agarose gel electrophoresis.

(Primer)

B1:
(SEQ ID NO: 95)
5'-TACATCAGCTTCCAGCCACCTATGATGTACCCCCACCCC-3'

C1:
(SEQ ID NO: 96)
5'-TACATCAGCTTCCAGATGATGTACCCCCACCCCGCCTAT-3'

D1:
(SEQ ID NO: 97)
5'-TACATCAGCTTCCAGTACCCCCACCCCGCCTATCCGATG-3'

E1:
(SEQ ID NO: 98)
5'-TACATCAGCTTCCAGCCCCACCCCGCCTATCCGATGCCT-3'

F1:
(SEQ ID NO: 99)
5'-TACATCAGCTTCCAGCACCCCGCCTATCCGATGCCTTTC-3'

G1:
(SEQ ID NO: 100)
5'-TACATCAGCTTCCAGCCCGCCTATCCGATGCCTTTCATC-3'

H1:
(SEQ ID NO: 101)
5'-TACATCAGCTTCCAGGCCTATCCGATGCCTTTCATCACC-3'

I1:
(SEQ ID NO: 102)
5'-TACATCAGCTTCCAGTATCCGATGCCTTTCATCACCACC-3'

J1:
(SEQ ID NO: 103)
5'-TACATCAGCTTCCAGCCGATGCCTTTCATCACCACCATT-3'

K1:
(SEQ ID NO: 104)
5'-TACATCAGCTTCCAGCCTTTCATCACCACCATTCTGGGA-3'

Next, the polynucleotide (NCRD) which encodes the NCRD and the respective polynucleotides (CCRD 1 to CCRD 10) which encodes the CCRDs were mixed, these mixtures were subjected to second stage PCR using the primers A1 and A4, and the obtained PCR products were purified by agarose gel electrophoresis. The purified PCR products were cleaved by restriction enzymes NdeI and BamHI and purified, the resultants were then each ligated to a pET-11a vector that has been cleaved by the same restriction enzyme, and clones containing correct sequences were then selected in the usual manner. These clones were used as the expression vectors for the respective galectin-9 variants.

(Primer)

A4:
(SEQ ID NO: 105)
5'-CGACCGGGATCCCTATGTCTGCACATGGGTCAGCTG-3'

The clones were then each transfected into *E. coli* BL21 (DE3) to produce transformants for recombinant protein expression, and the transformants were stored at −80° C. in the presence of about 15% glycerin.

(1-2) Deletion and Substitution Type Galectin-9 Variant

As galectin-9 variants, proteins were designed by substituting amino acids in the N-terminal region of the CCRD of the galectin-9 variants mC9 to mC12. The types of, the amino acid sequences and base sequences of the N-terminal regions of, and full-length amino acid sequences and full-length base sequences of the respective galectin-9 variants are summarized below. In the following sequences, the underlined portions indicate the amino acid residues substituted for the corresponding amino acid residues of the amino acid sequences of mC9 to mC12.

TABLE 6

|  | N-terminal region in CCRD | | | Full-length | |
| --- | --- | --- | --- | --- | --- |
|  | Amino acid sequence | Amino acid SEQ ID NO | Base SEQ ID NO | Amino acid SEQ ID NO | Base SEQ ID NO |
| mC9 | PHPAYPMP | 8 | 50 | 36 | 78 |
| mC9-HP | HPPAYPMP | 9 | 51 | 37 | 79 |
| mC10 | HPAYPMP | 10 | 52 | 38 | 80 |
| mC10-1P1A1 | HAAYPMP | 11 | 53 | 39 | 81 |
| mC10-1P1A2 | HPAYAMP | 12 | 54 | 40 | 82 |
| mC10-HPAP | HPAPPMP | 13 | 55 | 41 | 83 |
| mC10-HPPY | HPPYPMP | 14 | 56 | 42 | 84 |
| mC11 | PAYPMP | 15 | 57 | 43 | 85 |
| mC11-AP | APYPMP | 16 | 58 | 44 | 86 |
| mC11-PP | PPYPMP | 17 | 59 | 45 | 87 |

The expression vectors that express the galectin-9 variants were constructed by the following method. First, with the expression vectors for mC9, mC10, mC11, and mC12 being used as target sequences, PCR using the primer A1 and the primers L2 to W2 each containing a mutant sequence corresponding to the substituted amino acid sequence was conducted, and the obtained PCR products were purified by agarose gel electrophoresis (muNCRD1 to muNCRD12, 12 types).

(Primer)
L2:
(SEQ ID NO: 106)
5'-ATAGGCGGGCGGGTGCTGGAAGCTGATGTAGGA-3'

M2:
(SEQ ID NO: 107)
5'-GATAGGCGGCGTGCTGGAAGCTGATGTA-3'

N2:
(SEQ ID NO: 108)
5'-AAGGCATCGCATAGGCGGGTGCTGGAA-3'

O2:
(SEQ ID NO: 109)
5'-TGATGAAAGCCATCGGATAGGCGGGGTG-3'

P2:
(SEQ ID NO: 110)
5'-TGATGAAAGCCATCGCATAGGCGGCGTGCTGGAAGCTGATG-3'

Q2:
(SEQ ID NO: 111)
5'-TGAAAGGCGGCGGATAGGGGGGGTGCTG-3'

R2:
(SEQ ID NO: 112)
5'-GGCATCGGCGGGCGGGTGCTGGAAGCT-3'

S2:
(SEQ ID NO: 113)
5'-TCGGATAGGGGGGGTGCTGGAAGCTGAT-3'

T2:
(SEQ ID NO: 114)
5'-CGGATAGGGGGCCTGGAAGCTGATGTAGGA-3'

U2:
(SEQ ID NO: 115)
5'-TCGGATAGGGGGGCTGGAAGCTGATGTA-3'

V2:
(SEQ ID NO: 116)
5'-TGGTGATGAAAGCCATCGCATAGGCCTGGAAGCTGAT-3'

W2:
(SEQ ID NO: 117)
5'-AGGCATCGGAGGGGCCTGGAAGCTGATGTA-3'

In the same manner, with the expression vectors for mC9, mC10, mC11, and mC12 being used as target sequences, PCR using the primer A4 and the primers L1 to W1 each containing a mutant sequence corresponding to the substituted amino acid sequence was conducted, and the obtained PCR products were purified by agarose gel electrophoresis (muCCRD1 to muCCRD12, 12 types).

(Primer)
L1:
(SEQ ID NO: 118)
5'-AGCTTCCAGCACCCGCCCGCCTATCCGATGCCT-3'

M1:
(SEQ ID NO: 119)
5'-TTCCAGCACGCCGCCTATCCGATGCCTT-3'

N1:
(SEQ ID NO: 120)
5'-CCCGCCTATGCGATGCCTTTCATCACCA-3'

O1:
(SEQ ID NO: 121)
5'-TATCCGATGGCTTTCATCACCACCATTC-3'

P1:
(SEQ ID NO: 122)
5'-TTCCAGCACGCCGCCTATGCGATGGCTTTCATCACCACCATTC-3'

Q1:
(SEQ ID NO: 123)
5'-CTATCCGCCGCCTTTCATCACCACCATT-3'

R1:
(SEQ ID NO: 124)
5'-CCCCGCCCCGCCGATGCCTTTCATCACC-3'

S1:
(SEQ ID NO: 125)
5'-CAGCACCCCCCCTATCCGATGCCTTTCA-3'

T1:
(SEQ ID NO: 126)
5'-TTCCAGGCCCCCTATCCGATGCCTTTCA-3'

U1:
(SEQ ID NO: 127)
5'-CCAGCCCCCCTATCCGATGCCTTTCATC-3'

V1:
(SEQ ID NO: 128)
5'-TTCCAGGCCTATGCGATGGCTTTCATCACCACCATTC-3'

W1:
(SEQ ID NO: 129)
5'-TTCCAGGCCCCTCCGATGCCTTTCATCACC-3'

Next, the former PCR products (muNCRD1 to muNCRD12) and the latter PCR products (muCCRD1 to muCCRD12) were mixed, these mixtures were amplified by second stage PCR using the primers A1 and A4, and the obtained PCR products were purified by agarose gel electrophoresis. The purified PCR products were cleaved by restriction enzymes NdeI and BamHI and purified, the resultants were then each ligated to a pET-11a vector that has been cleaved by the same restriction enzyme, and clones containing correct sequences were then selected in the usual manner. These clones were used as the expression vectors for the respective galectin-9 variants.

The clones were then each transfected into E. coli BL21 (DE3) to produce transformants, and the transformants were stored at −80° C. in the presence of about 15% glycerin.

(2) Measurement of Expression and Yield of Galectin-9 Variant

Galectin-9 variants were expressed by the following method using the transformants produced in the item (1) above, and the yields were measured with respect to test samples of recombinant proteins right after expression (also referred to as preparations right after expression) and test samples of recombinant proteins from which insoluble matters were removed after three months storage after expression (also referred to as preparations after three months storage).

The transformants were each added to LB-broth that contains 100 µg/mL ampicillin and cultured at 37° C. overnight. 400 mL of 2XYT, 4 mL of 10 mg/mL ampicillin, and 8 mL of each of E. coli culture solutions obtained by the culture were added to 1000 mL flask. Subsequently, the resultants were each cultured at 37° C. while shaking the flask until A600 nm becomes about 0.7. 0.4 mL of 0.1 mol/L isopropyl-β-D(−)thiogalactopyranoside (IPTG) was then added to each of the flasks and the resultants were cultured at 20° C. overnight (16 to 20 hours). Bacterial cells were then recovered from the culture solutions by centrifugation.

The recovered bacterial cells were suspended in the flasks each containing 80 mL of buffer solution for extraction. The buffer solution for extraction had the following composition: 10 mmol/L Tris-HCl (pH7.5), 0.5 mol/L NaCl, 1 mmol/L dithiothreitol (DTT), 1 mmol/L phenylmethylsulfonyl fluoride (PMSF), and 1% Triton X-100. Each of the suspensions was then sonicated under the following conditions: output control=5 and % duty cycle=100. Thereafter, the resultants were stirred at 4° C. for 30 minutes. With regard to the sonication, one cycle of the treatment for 2 minutes and the pause for 1 minute was repeated for a total of four cycles. Subsequently, the suspensions were subjected to the centrifugation at 15,000×g for 30 minutes to remove insoluble matters, and thereby recovered supernatants.

3 mL of lactose-agarose suspension (50% [v/v] in PBS, 1.5 ml as a gel) was added to each of the obtained supernatants, and the resultants were stirred at 4° C. for 1 hour. The resultants were then each subjected to the centrifugation at 2,000×g for 5 minutes to recover lactose-agarose gel, and the recovered lactose-agarose gels were each suspended in TBS that contains 0.03% 3-[(3-cholamidopropyl)dimethylammonio]propanesulfonate (CHAPS) and then charged in a minicolumn. Subsequently, after washing each gel with TBS that contains 0.03% CHAPS in an amount of 10 times the amount of the gel, protein was eluted with 3 mL of eluate. The elute had the following composition: 20 mmol/L Tris-HCl (pH7.5), 0.15 mol/L NaCl, and 0.2 mol/L lactose. The respective elutes were dialyzed against PBS, then subjected to the centrifugation at 25,000×g for 20 minutes to remove insoluble matters, and the supernatants thereby obtained were filter sterilized to obtain final samples. Hereinafter, these will be referred to as test samples right after preparation. 3 μg of each sample was subjected to SDS-PAGE and stained with coomassie brilliant blue R-250. In the usual manner, the purity test of protein and the concentration measurement of protein by SDS-PAGE were then performed, and the yield of each galectin-9 variant was calculated. This was considered as the yield of recombinant protein right after preparation.

Also the test samples right after preparation were stored at 4° C. for 3 months. After the storage, the samples were subjected to the centrifugation at 25,000×g for 20 minutes to remove insoluble matters, and the supernatants thereby obtained were filter sterilized to obtain test samples after 3 months storage. In the same manner as the test samples right after preparation, the concentration of each protein was then measured, and the yield of each galectin-9 variant was calculated in the usual manner. This was considered as the yield of recombinant protein after 3 months storage.

Also, as a comparative example, using the expression vector ET-G9Null for the stabilized galectin-9, the expression and evaluation of protein were performed in the same manner.

FIG. 2 shows the photograph of SDS-PAGE. In FIG. 2, the lane M indicates molecular weight markers, and each lane indicates the test sample right after preparation of each galectin-9 variant. As shown in FIGS. 2 and 3, it was verified that all galectin-9 variants can be expressed in *Escherichia coli* and can be highly purified by affinity chromatography using lactose-agarose.

FIG. 3 shows the concentrations of the deletion type galectin-9 variants prepared in the item (1-1) above and the stabilized galectin-9. In FIG. 3, A indicates the results of the test samples right after preparation and B indicates the results of the test samples after 3 months storage. In FIG. 3, each of the vertical axes indicates the concentration (μg/ml) of the galectin-9 variant or the stabilized galectin-9 in the sample; and the average value of two expression experiments is shown with respect to each galectin-9 variant and the average value and standard deviation of twelve expression experiments are shown with respect to the stabilized galectin-9.

As shown in FIG. 3, with respect to the test samples right after preparation, the galectin-9 variants mC8, mC9, mC10, mC11, mC12, mC13, and mC14 each showed higher protein concentration than the stabilized galectin-9 (G9Null). Among others, mC9, mC10, mC12 and mC14 each showed very high protein concentration. Also with respect to the test samples after 3 months storage, the galectin-9 variants mC10, mC11, mC12, and mC13 each showed significantly higher protein concentration than the stabilized galectin-9 (G9Null).

Since the stabilized galectin-9 (G9Null) exceeded its maximum solubility in the elution step from the column at the time of preparing a final sample after expression (test sample right after preparation), a part of the stabilized galectin-9 was insolubilized. This insoluble matter was removed by the centrifugation step and the filtration step after the elution step.

Therefore, as shown in FIG. 3, the stabilized galectin-9 showed a low protein concentration in the test sample as mentioned above. On the other hand, the insolubilization in the elution step of each galectin-9 variant was significantly suppressed as compared to the stabilized galectin-9. Therefore, as shown in FIG. 3, the galectin-9 variants showed significantly high protein concentrations in the test samples as compared to the stabilized galectin-9.

In the present example, with respect to all recombinant proteins, fixed-volume final samples (test samples right after preparation) were prepared under the same conditions. Therefore, the fact that the concentration of each galectin-9 variant in the test sample is significantly higher than that of the stabilized galectin-9 in the test sample means that the solubility of each galectin-9 variant is significantly higher than that of the stabilized galectin-9. Also the high concentration of each galectin-9 variant in the test sample means that each galectin-9 variant was recovered with high yield.

In the synthesis of a target protein, the purification of the protein involving centrifugal treatment, filtration treatment, and the like, and the pharmaceutical preparation of the protein, generally, the solubilization of the protein is utilized with respect to an aqueous solvent such as a buffer solution. Therefore, the higher the solubility of the protein is, the less the loss of the protein in recovery becomes, for example. Also the higher solubility of the protein results in superior handleability. Since the galectin-9 variants according to the present invention are superior in solubility as mentioned above, it can be said that they are superior in the production, purification, and pharmaceutical preparation of protein as compared to the stabilized galectin-9 having the same bioactivity.

Figure 4:
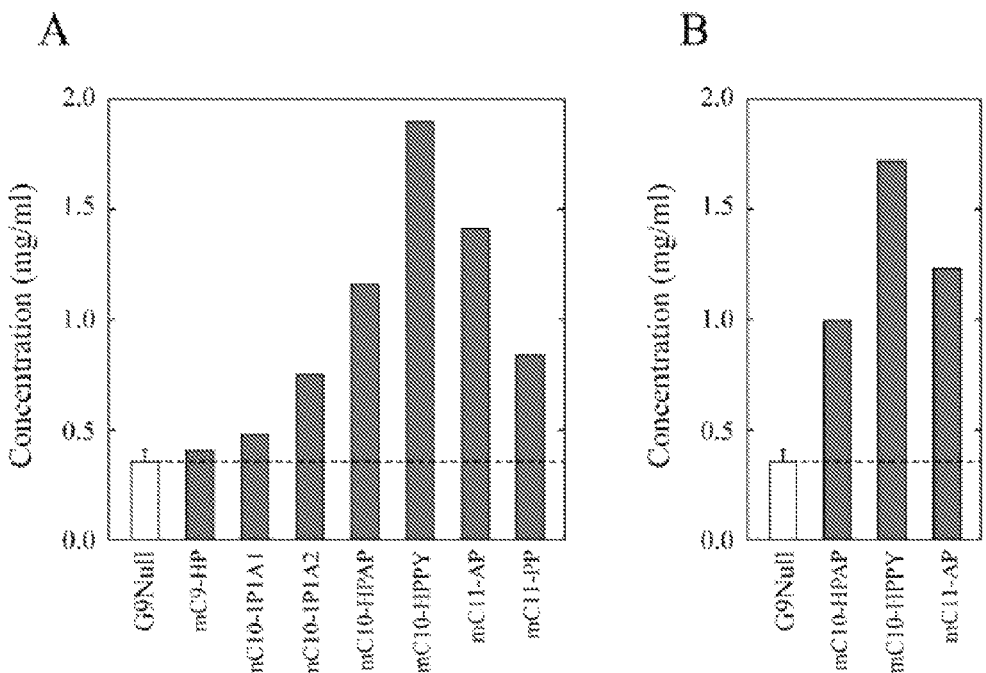
FIG. 4 shows graphs showing concentrations of the deletion and substitution-type galectin-9 variant in Example 1 of the present invention.

FIG. 4 shows the concentrations of the deletion and substitution type galectin-9 variants prepared in the item (1-2) above and the deletion type galectin-9 variants prepared in the item (1-1) above. In FIG. 4, A indicates the results of the test samples right after preparation and B indicates the results of the test samples after 3 months storage. In FIG. 4, each of the vertical axes indicates the concentration (μg/ml) of the galectin-9 variant in the test sample; and the average value of two expression experiments is shown with respect to each galectin-9 variant and the average value and standard deviation of twelve expression experiments are shown with respect to the stabilized galectin-9.

As shown in FIG. 4, with respect to the test samples right after preparation, the deletion and substitution type galectin-9 variants mC9-HP, mC10-1P1A1, mC10-1P1A2, mC10-HPAP, mC10-HPPY, mC11-AP, and mC11-PP each showed higher protein concentration than the stabilized galectin-9. Also with respect to the test samples after 3 months storage, deletion and substitution type galectin-9 variants mC10-HPAP, mC10-HPPY, and mC11-AP each showed higher protein concentration than the stabilized galectin-9.

Furthermore, as shown in FIG. 4, with respect to the test samples right after preparation, the deletion and substitution type galectin-9 variants mC10-HPAP, mC10-HPPY, mC11-AP, and mC11-PP respectively showed higher protein concentrations than the corresponding deletion type galectin-9 variants. Also with respect to the test samples after 3 months storage, the deletion and substitution type galectin-9 variants mC10-HPPY and mC11-AP respectively showed higher protein concentrations than the corresponding galectin-9 variants. Among others, in the case of comparing the test samples after 3 months storage, the protein concentration of the deletion and substitution type mC10-HPPY in which proline residues were conserved and tyrosine residues were substituted with proline residues was increased about 3.3 times the protein concentration of the deletion type mC10. Also the protein concentration of the deletion and substitution type mC11-AP in which proline-alanine was substituted with alanine-proline was increased about 2.2 times the protein concentration of the deletion type mC11. From these results, it was found that the solubility of the galectin-9 variant can be further improved by conservation of proline residues at position 12 or 15 and position 17 of SEQ ID NO: 3 and further substitution for proline residues in the N-terminal region of the CCRD.

(3) Measurement of Apoptosis Induction Activity of Galectin-9 Variant to Jurkat Cell Jurkat cells cultured in a RPMI1640-10% FBS culture medium were recovered by centrifugation and suspended in a new culture medium so as to achieve a concentration of $3\times10^4$ cells/90 μL. 90 μL of the obtained suspension was seeded into each well of a 96-well plate. After the cells were cultured for 3 hours in a $CO_2$ incubator, 10 μL of each of the samples containing galectin-9 variants was then added to each well. The samples were prepared by diluting the respective galectin-9 variants of the item (1) above with PBS so as to achieve concentrations of 0.01, 0.03, 0.1, 0.3, and 1 μmol/L in the respective wells. Next, after the cells were cultured for 24 hours, 10 μL of WST-8 reagent was added to each well, and the cells were further cultured for 3 hours. 10 μL of 1.2% SDS was then added to each well, the absorbance of each well at the wavelengths of 450 nm and 620 nm was measured using a microplate reader, and the difference between the absorbance at 450 nm and the absorbance at 620 nm was calculated. This assay was performed with three wells as one set. Also, as a control, the same measurement was performed by adding 10 μl of PBS instead of the samples. With the calculated value of the control being considered as 100%, the relative values (%) with respect to the calculated values in the cases of adding the samples were then obtained. These relative values were considered as the values showing the number of cells.

Also, as a comparative example, the number of cells was measured in the same manner using the stabilized galectin-9 (G9Null) instead of the galectin-9 variants.

From these results, the concentrations (LD 50) of the galectin-9 variants and the stabilized galectin-9 which cause 50% decrease of the number of Jurkat cells were obtained. With the LD 50 of the stabilized galectin-9 being considered as 100%, the relative values (%) of the respective galectin-9 variants were obtained as specific activities. The results are shown in Table 7.

TABLE 7

|  |  | Apoptosis induction activity (%) |
|---|---|---|
| Stabilized galectin-9 | G9Null | 100 |
| Galectin-9 variant | mC6 | 170 |
|  | mC8 | 130 |
|  | mC9 | 190 |
|  | mC10 | 190 |
|  | mC11 | 210 |
|  | mC12 | 230 |
|  | mC13 | 120 |
|  | mC10-HPPY | 250 |
|  | mC10-HPAP | 120 |
|  | mC11-AP | 190 |

As can be seen from Table 7, the galectin-9 variants each showed significantly higher apoptosis induction activity to Jurkat cells than the stabilized galectin-9 (G9Null). From this result, it was found that the galectin-9 variants sufficiently maintain the bioactivity of the stabilized galectin-9 and are superior in solubility as mentioned above.

(4) Protease Stability

With respect to the galectin-9 variant mC10-HPPY prepared in the item (2) above, the stability to protease present in human tissues was examined.

The galectin-9 variant was dissolved in 100 mmol/L Tris-HCl (pH8.0) that contains 150 mmol/L NaCl and 1 mmol/L $CaCl_2$ at a concentration of 0.06 mg/mL, and further, protease was mixed thereto, followed by incubation at 37° C. The proportion of protease (P) to be added to the galectin-9 variant (G) was G:P=100:1 in weight ratio. As the protease, elastase (trade name: Elastase (product of Elastin Products Company, Inc.)) or matrix metalloproteinase-3 (MMP-3, trade name: Matrix Metalloproteinase-3 (product of Biogenesis)) was used. MMP-3 was activated by activation treatment at 37° C. for 8 hours using 20 mmol/L Aminophenyl mercuric acetate before use. Sampling was performed over time during the incubation, and each sample was subjected to SDS-PAGE and stained with coomassie brilliant blue R-250. Also, as a comparative example, wild-type galectin-9 preparation (G9S, amino acid sequence of SEQ ID NO: 131) or the stabilized galectin-9 (G9Null) prepared in the item (2) above was used instead of the galectin-9 variant.

Figure 5:
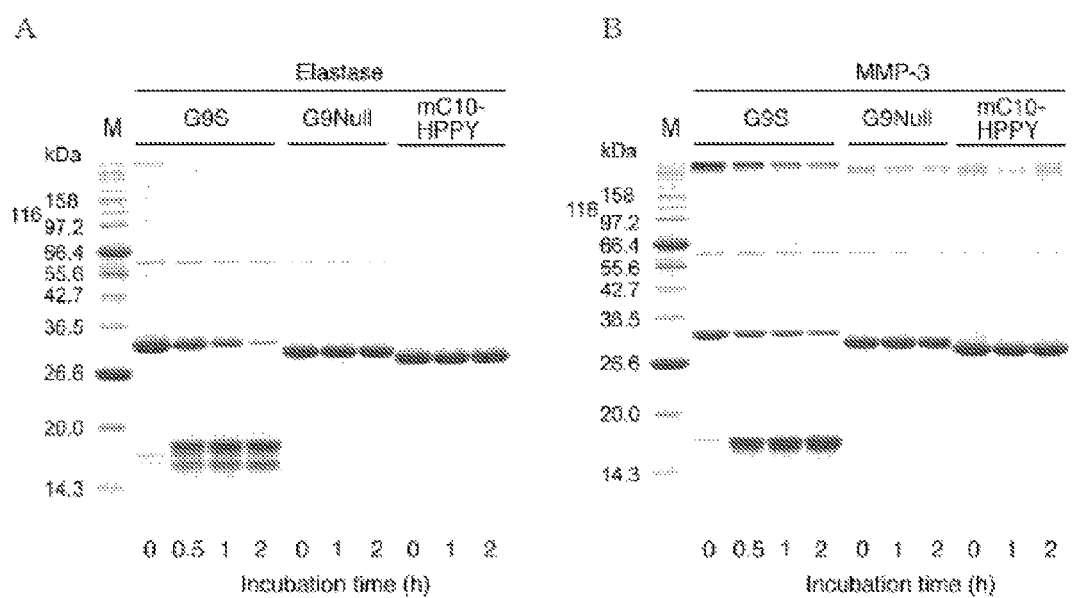
FIG. 5 shows graphs showing the protease stability in Example 1 of the present invention.

FIG. 5 shows the photographs of SDS-PAGE. In FIG. 5, A indicates the results obtained by using elastase and B indicates the results obtained by using MMP-3. In FIG. 5, the lane M indicates molecular weight markers. As shown in A and B of FIG. 5, degradation of wild-type G9S was recognized only 0.5 hours after the start of the incubation, and the wild-type G9S was mostly degraded in 2 hours. In contrast, degradation of the galectin-9 variant mC10-HPPY was not recognized even after 2 hours incubation as with the stabilized galectin-9 whose protease stability has been verified in WO2005/093064. From these results, it was confirmed that mC10-HPPY is also superior in protease stability. The same applies to other galectin-9 variants.

As described above, it was verified that each galectin-9 variant according to the present invention has superior solubility than the stabilized galectin-9, maintains the bioactivities of the wild-type galectin-9, and has superior protease stability than the wild-type galectin. Specifically, as described in the item (2) above, the solubility (i.e., yields) of all galectin-9 variants was significantly increased as compared to the stabilized galectin-9. Among others, the solubility (i.e., yields) of mC10, mC11, mC12, mC10-HPPY, mC10-HPAP, and mC11-AP was increased more than 5 times the solubility of the stabilized galectin-9. In particular, it was verified that mC10-HPPY could be present in a stable manner in PBS at least up to a concentration of 2.5 mg/mL, which is about 7 times the concentration of the stabilized galectin-9. Also, as described in the item (3) above, all galectin-9 variants showed the apoptosis induction activity to Jurkat cells, which is one of the bioactivities of the wild-type galectin-9. Among others, mC10, mC11, mC12, mC10-HPPY, mC10-HPAP, and mC11-AP each showed the activity 2 to 2.5 times the activity of the stabilized galectin-9. Furthermore, as described in the item (4) above, each of the galectin-9 variants showed significant protease stability as compared to the wild-type galectin-9. From these results, it can be said that the galectin-9 variants have excellent properties as medical materials of high productivity, and among others, mC10-HPPY has an excellent property.

Example 2

The present example examined the influence of long-term storage of the above galectin-9 variants on their solubility and the degranulation inhibitory activities of the galectin-9 variants against RBL-2H3 cells.

(1) Influence of Long-Term Storage on Solubility

Each of the galectin-9 variants was stored at 4° C. for about a year (344 days). Thereafter, the influence of this long-term storage on the solubility of the galectin-9 variant was examined.

The filter-sterilized test samples (the galectin-9 variants) prepared in the item (2) in Example 1 right after the preparation were stored at 4° C. for about a year (344 days). The protein concentration in each test sample was adjusted as follows: 1.88 mg/mL in mC10-HPPY; 1.16 mg/mL in mC10-HPAP, and 1.14 mg/mL in mC11-AP. Subsequently, the test sample after the storage was centrifuged at 25,000×g for 20 minutes. Insoluble matters were removed, and the supernatant was collected. The absorbance of each test sample after the one-year storage was measured at 280 nm, and the protein concentration was calculated. Assuming that the protein concentration of the galectin-9 variant in the test sample before the storage was 100%, the relative value (%) of the protein concentration of the galectin-9 variant in the test sample after the storage was then determined. The results thereof are shown in Table 8 below.

TABLE 8

| Galectin-9 variants | Protein concentration (proportion relative to that in test sample before storage, %) |
| --- | --- |
| mC10-HPPY | 100 |
| mC10-HPAP | 90 |

As can be seen from Table 8, the protein concentrations of mC10-HPPY and mC10-HPAP remained substantially the same even after the storage for about one year. It was thus found that mC10-HPPY and mC10-HPAP can maintain high solubility even after long-term storage.

(2) Measurement of Degranulation Inhibitory Activities of Galectin-9 Variants Against RBL-2H3 Cells RBL-2H3 cells cultured in a RPMI 1640-10% FBS medium were collected by trypsinization. The collected RBL-2H3 cells were then suspended in a fresh medium so as to achieve a cell density of $2\times10^4$ cells/100 μL. The thus-obtained suspension was seeded into a 96-well plate so that each well contained 100 μL of the suspension. Thereafter, the cells were cultured for 24 hours in a $CO_2$ incubator".

Each well was washed once with an activity measurement buffer solution (Hanks' balanced salt solution containing 20 mmol/L HEPES-NaOH (pH 7.5) and 1 mg/mL bovine serum albumin). To each well, 90 μL of the activity measurement buffer solution was then added, and further, 10 μL of each of samples containing the above-described galectin-9 variants was added. The samples were prepared by diluting each galectin-9 variant used in the item (1) in Example 1 with PBS so that the concentration of the galectin-9 variant in each well was 0.1, 0.25, 0.5, 0.75, or 1 μmol/L. Subsequently, the 96-well plate was allowed to stand still for 10 minutes, and anti-2,4,6-trinitrophenyl (TNP) mouse monoclonal antibody (IgE) and TNP-labeled bovine serum albumin were then added so that their concentrations in each well were 0.3 μg/mL and 0.048 μg/mL, respectively. The resultant mixture was cultured for 1 hour. Thereafter, the medium was collected from each well, and the cultured cells were then lysed using 0.1% Triton X-100. The β-hexaminidase (β-HEX) activity was measured in the collected medium and in the cell lysate. The total of the β-HEX activity in the medium and the β-HEX activity in the cell lysate was calculated as a total β-HEX activity. The proportion (%) of the β-HEX activity in the medium to the total β-HEX activity was then determined. The thus-determined proportion was used as an index of degranulation. This assay was performed with three wells as one set.

Furthermore, the measurement was performed in the same manner, except that: as a control, 10 μL of PBS was added instead of the sample; and as a comparative example, the stabilized galectin-9 (G9Null) in Example 1 was added instead of the galectin-9 variant.

From the results thereof, the concentration (LD50) at which each of the galectin-9 variants and the stabilized galectin-9 decreased the degranulation of the RBL-2H3 cells by 50% was determined. Assuming that LD50 of the stabilized galectin-9 was 100%, the relative values (%) of LD50 of the respective galectin-9 variants were then determined as the degranulation inhibitory activities (%). The results thereof are shown in Table 9 below.

TABLE 9

|  |  | Degranulation inhibitory activity (%) |
| --- | --- | --- |
| Stabilized galectin-9 | G9Null | 100 |
| Galectin-9 variants | mC6 | 94 |
|  | mC8 | 180 |
|  | mC9 | 160 |
|  | mC10 | 250 |
|  | mC11 | 170 |
|  | mC12 | 190 |
|  | mC13 | 190 |
|  | mC10-HPPY | 150 |
|  | mC10-HPAP | 170 |
|  | mC11-AP | 170 |

As can be seen from Table 9, all the galectin-9 variants exhibited degranulation inhibitory activities against the RBL-2H3 cells, similarly to the stabilized galectin-9 (G9 Null). In particular, mC8, mC9, mC10, mC11, mC12, mC13, mC10-HPPY, mC10-HPAP, and mC11-AP exhibited significantly high degranulation inhibitory activities, as compared with the stabilized galectin-9 (G9Null). From these results, it was found that the galectin-9 variants sufficiently conserve the physiological activities of the stabilized galectin-9.

As specifically described above, it was confirmed that the galectin-9 variant according to the present invention maintains high solubility even after long-term storage. It was also confirmed that the galectin-9 variant according to the present invention conserves the physiological activities of the wild-type galectin 9. More specifically, as described in the item (1) above, all the galectin-9 variants exhibited substantially the same protein concentrations even after the storage for about a year, and maintained high solubility after long-term storage. Also, as described in the item (2) above, all the galectin-9 variants maintained degranulation inhibitory activity against RBL-2H3 cells, which is one of the physiological activities of the wild-type galectin 9. In particular, the degranulation inhibitory activities of mC8, mC9, mC10, mC11, mC12, mC13, mC10-HPPY, mC10-HPAP and mC11-AP were 1.5 to 2.5 times higher than that of the stabilized galectin-9. From these results, it can be said that the galectin-9 variant is stable and has excellent properties as a raw material of pharmaceuticals.

While the present invention has been described above with reference to illustrative embodiments and examples, the present invention is by no means limited thereto. Various changes and modifications that may become apparent to those skilled in the art may be made in the configuration and specifics of the present invention without departing from the scope of the present invention.

This application claims priority from Japanese Patent Application No. 2012-254349 filed on Nov. 20, 2012. The entire subject matter of the Japanese Patent Application is incorporated herein by reference.

INDUSTRIAL APPLICABILITY

As described above, the galectin-9 variant according to the present invention has the same bioactivity as wild-type galectin 9, is superior in protease stability and solubility, and is also superior in yield at the time of producing as a recombinant protein. As described above, the galectin-9 variant according to the present invention not only has bioactivity of wild-type galectin, but also is superior in stability, handleability, and yield in production. Thus, it can be said that the galectin-9 variant according to the present invention is really useful as a pharmaceutical material.

SEQUENCE LISTING

TF13029WO_ST25.txt

---

The invention claimed is:

1. A protein or a salt thereof, consisting of:
NCRD; and
CCRD, a C terminus of the NCRD and an N terminus of the CCRD being directly bound to each other, wherein:
the NCRD is
(N1) a peptide consisting of an amino acid sequence represented by SEQ ID NO: 1, or
(N2) a peptide consisting of an amino acid sequence obtained by deletion, substitution and/or insertion of between 1 and 15 amino acid residues in the amino acid sequence represented by SEQ ID NO: 1 and has a carbohydrate binding ability, and
the CCRD is
a peptide consisting of an N-terminal region and a C-terminal region and having a carbohydrate binding ability, wherein:
the N-terminal region is (C-N1) a peptide consisting of an amino acid sequence obtained by deletion of between 8 and 14 amino acid residues in an amino acid sequence of SEQ ID NO: 3, and
the C-terminal region is
(C-C1) a peptide consisting of an amino acid sequence represented by SEQ ID NO: 5, or
(C-C2) a peptide consisting of an amino acid sequence obtained by deletion, substitution and/or insertion of between 1 and 13 amino acid residues in the amino acid sequence of SEQ ID NO: 5.

2. The protein or a salt thereof according to claim 1, wherein
the deletion of the amino acids in the N-terminal region of the CCRD is a deletion of consecutive amino acids or inconsecutive amino acids.

3. The protein or a salt thereof according to claim 1, wherein
the deletion of the amino acids in the N-terminal region of the CCRD is a deletion of consecutive amino acids.

4. The protein or a salt thereof according to claim 3, wherein
the deletion of the amino acids in the N-terminal region of the CCRD is a deletion of consecutive amino acids from the N terminus.

5. The protein or a salt thereof according claim 1, wherein
at least one amino acid residue selected from the group consisting of 10th, 11th, 12th, 13th, 15th, and 17th amino acids in the amino acid sequence of SEQ ID NO: 3 of the peptide (C-N1) is proline.

6. The protein or a salt thereof according to claim 1, wherein
10th and 11th amino acid residues in the amino acid sequence of SEQ ID NO: 3 of the peptide (C-N1) are Pro-Pro, Pro-His, or His-Pro.

7. The protein or a salt thereof according to claim 1, wherein
12th and 13th amino acid residues in the amino acid sequence of SEQ ID NO: 3 of the peptide (C-N1) are Pro-Pro, Pro-Ala, or Ala-Pro.

8. The protein or a salt thereof according to claim 1, wherein
the N-terminal region in the CCRD is a peptide composed of any one of amino acid sequences of SEQ ID NOs: 7 to 20.

9. The protein or a salt thereof according to claim 1, wherein
the CCRD is a peptide composed of any one of amino acid sequences of SEQ ID NOs: 21 to 34.

10. The protein or a salt thereof according to claim 1, consisting of any one of amino acid sequences of SEQ ID NOs: 35 to 48.

11. A nucleic acid comprising a nucleotide sequence which encodes the protein according to claim 1.

12. An expression vector comprising the nucleic acid according to claim 11.

13. A transformant comprising a nucleic acid comprised of a base sequence which encodes the protein according to claim 1 or an expression vector comprising the nucleic acid comprised of a base sequence which encodes the protein according to claim 1.

* * * * *

SEQUENCE LISTING

```
<160> NUMBER OF SEQ ID NOS: 132

<210> SEQ ID NO 1
<211> LENGTH: 148
<212> TYPE: PRT
<213> ORGANISM: Artificial Sequence
<220> FEATURE:
<223> OTHER INFORMATION: artificially synthesized sequence

<400> SEQUENCE: 1

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
                20                  25                  30

Val Asn Gly Thr Val Leu Ser Ser Ser Gly Thr Arg Phe Ala Val Asn
            35                  40                  45

Phe Gln Thr Gly Phe Ser Gly Asn Asp Ile Ala Phe His Phe Asn Pro
        50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
                100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
        130                 135                 140

Ile Ser Phe Gln
145
```

<210> SEQ ID NO 2
<211> LENGTH: 444
<212> TYPE: DNA
<213> ORGANISM: Artificial Sequence
<220> FEATURE:
<223> OTHER INFORMATION: artificially synthesized sequence

<400> SEQUENCE: 2

```
atggccttca gcggttccca ggctccctac ctgagtccag ctgtcccctt ttctgggact      60
attcaaggag gtctccagga cggacttcag atcactgtca atgggaccgt tctcagctcc     120
agtggaacca ggtttgctgt gaactttcag actggcttca gtggaaatga cattgccttc     180
cacttcaacc ctcggtttga agatggaggg tacgtggtgt gcaacacgag cagaacggga     240
agctgggggc ccgaggagag gaagacacac atgccttttc cagaagggga tgcccttgac     300
ctctgcttcc tggtgcagag ctcagatttc aaggtgatgg tgaacggtat cctcttcgtg     360
cagtacttcc accgcgtgcc cttccaccgt gtggacacca tctccgtcaa tggctctgtg     420
cagctgtcct acatcagctt ccag                                            444
```

<210> SEQ ID NO 3
<211> LENGTH: 17
<212> TYPE: PRT
<213> ORGANISM: Artificial Sequence
<220> FEATURE:
<223> OTHER INFORMATION: artificially synthesized sequence
<220> FEATURE:
<221> NAME/KEY: misc_feature
<222> LOCATION: (10)..(11)
<223> OTHER INFORMATION: Xaa is Pro or His
<220> FEATURE:
<221> NAME/KEY: misc_feature
<222> LOCATION: (12)..(13)
<223> OTHER INFORMATION: Xaa is Pro or Ala

<400> SEQUENCE: 3

Thr Pro Ala Ile Pro Pro Met Met Tyr Xaa Xaa Xaa Xaa Tyr Pro Met
1               5                   10                  15

Pro

<210> SEQ ID NO 4
<211> LENGTH: 51
<212> TYPE: DNA
<213> ORGANISM: Artificial Sequence
<220> FEATURE:
<223> OTHER INFORMATION: artificially synthesized sequence
<220> FEATURE:
<221> NAME/KEY: misc_feature
<222> LOCATION: (28)..(39)
<223> OTHER INFORMATION: n is a, c, g, or t

<400> SEQUENCE: 4

```
actcccgcca tcccacctat gatgtacnnn nnnnnnnnnt atccgatgcc t               51
```

<210> SEQ ID NO 5
<211> LENGTH: 129
<212> TYPE: PRT
<213> ORGANISM: Artificial Sequence
<220> FEATURE:
<223> OTHER INFORMATION: artificially synthesized sequence

<400> SEQUENCE: 5

Phe Ile Thr Thr Ile Leu Gly Gly Leu Tyr Pro Ser Lys Ser Ile Leu
1               5                   10                  15

Leu Ser Gly Thr Val Leu Pro Ser Ala Gln Arg Phe His Ile Asn Leu
            20                  25                  30

```
Cys Ser Gly Asn His Ile Ala Phe His Leu Asn Pro Arg Phe Asp Glu
            35                  40                  45
Asn Ala Val Val Arg Asn Thr Gln Ile Asp Asn Ser Trp Gly Ser Glu
 50                  55                  60
Glu Arg Ser Leu Pro Arg Lys Met Pro Phe Val Arg Gly Gln Ser Phe
 65                  70                  75                  80
Ser Val Trp Ile Leu Cys Glu Ala His Cys Leu Lys Val Ala Val Asp
                 85                  90                  95
Gly Gln His Leu Phe Glu Tyr Tyr His Arg Leu Arg Asn Leu Pro Thr
                100                 105                 110
Ile Asn Arg Leu Glu Val Gly Gly Asp Ile Gln Leu Thr His Val Gln
            115                 120                 125
Thr
```

```
<210> SEQ ID NO 6
<211> LENGTH: 390
<212> TYPE: DNA
<213> ORGANISM: Artificial Sequence
<220> FEATURE:
<223> OTHER INFORMATION: artificially synthesized sequence

<400> SEQUENCE: 6
ttcatcacca ccattctggg agggctgtac ccatccaagt ccatcctcct gtcaggcact    60
gtcctgccca gtgctcagag gttccacatc aacctgtgct ctgggaacca catcgccttc   120
cacctgaacc cccgttttga tgagaatgct gtggtccgca cacccagat cgacaactcc    180 tgggggtctg aggagcgaag tctgccccga aaaatgccct tcgtccgtgg ccagagcttc   240
tcagtgtgga tcttgtgtga agctcactgc ctcaaggtgg ccgtggatgg tcagcacctg   300
tttgaatact accatcgcct gaggaacctg cccaccatca acagactgga agtgggggc    360 gacatccagc tgacccatgt gcagacatag                                    390
```

```
<210> SEQ ID NO 7
<211> LENGTH: 9
<212> TYPE: PRT
<213> ORGANISM: Artificial Sequence
<220> FEATURE:
<223> OTHER INFORMATION: artificially synthesized sequence

<400> SEQUENCE: 7

Tyr Pro His Pro Ala Tyr Pro Met Pro
 1               5
```

```
<210> SEQ ID NO 8
<211> LENGTH: 8
<212> TYPE: PRT
<213> ORGANISM: Artificial Sequence
<220> FEATURE:
<223> OTHER INFORMATION: artificially synthesized sequence

<400> SEQUENCE: 8

Pro His Pro Ala Tyr Pro Met Pro
 1               5
```

```
<210> SEQ ID NO 9
<211> LENGTH: 8
<212> TYPE: PRT
<213> ORGANISM: Artificial Sequence
<220> FEATURE:
<223> OTHER INFORMATION: artificially synthesized sequence
```

```
<400> SEQUENCE: 9

His Pro Pro Ala Tyr Pro Met Pro
1               5

<210> SEQ ID NO 10
<211> LENGTH: 7
<212> TYPE: PRT
<213> ORGANISM: Artificial Sequence
<220> FEATURE:
<223> OTHER INFORMATION: artificially synthesized sequence

<400> SEQUENCE: 10

His Pro Ala Tyr Pro Met Pro
1               5

<210> SEQ ID NO 11
<211> LENGTH: 7
<212> TYPE: PRT
<213> ORGANISM: Artificial Sequence
<220> FEATURE:
<223> OTHER INFORMATION: artificially synthesized sequence

<400> SEQUENCE: 11

His Ala Ala Tyr Pro Met Pro
1               5

<210> SEQ ID NO 12
<211> LENGTH: 7
<212> TYPE: PRT
<213> ORGANISM: Artificial Sequence
<220> FEATURE:
<223> OTHER INFORMATION: artificially synthesized sequence

<400> SEQUENCE: 12

His Pro Ala Tyr Ala Met Pro
1               5

<210> SEQ ID NO 13
<211> LENGTH: 7
<212> TYPE: PRT
<213> ORGANISM: Artificial Sequence
<220> FEATURE:
<223> OTHER INFORMATION: artificially synthesized sequence

<400> SEQUENCE: 13

His Pro Ala Pro Pro Met Pro
1               5

<210> SEQ ID NO 14
<211> LENGTH: 7
<212> TYPE: PRT
<213> ORGANISM: Artificial Sequence
<220> FEATURE:
<223> OTHER INFORMATION: artificially synthesized sequence

<400> SEQUENCE: 14

His Pro Pro Tyr Pro Met Pro
1               5

<210> SEQ ID NO 15
<211> LENGTH: 6
<212> TYPE: PRT
<213> ORGANISM: Artificial Sequence
<220> FEATURE:
<223> OTHER INFORMATION: artificially synthesized sequence
```

```
<400> SEQUENCE: 15

Pro Ala Tyr Pro Met Pro
1               5

<210> SEQ ID NO 16
<211> LENGTH: 6
<212> TYPE: PRT
<213> ORGANISM: Artificial Sequence
<220> FEATURE:
<223> OTHER INFORMATION: artificially synthesized sequence

<400> SEQUENCE: 16

Ala Pro Tyr Pro Met Pro
1               5

<210> SEQ ID NO 17
<211> LENGTH: 6
<212> TYPE: PRT
<213> ORGANISM: Artificial Sequence
<220> FEATURE:
<223> OTHER INFORMATION: artificially synthesized sequence

<400> SEQUENCE: 17

Pro Pro Tyr Pro Met Pro
1               5

<210> SEQ ID NO 18
<211> LENGTH: 5
<212> TYPE: PRT
<213> ORGANISM: Artificial Sequence
<220> FEATURE:
<223> OTHER INFORMATION: artificially synthesized sequence

<400> SEQUENCE: 18

Ala Tyr Pro Met Pro
1               5

<210> SEQ ID NO 19
<211> LENGTH: 4
<212> TYPE: PRT
<213> ORGANISM: Artificial Sequence
<220> FEATURE:
<223> OTHER INFORMATION: artificially synthesized sequence

<400> SEQUENCE: 19

Tyr Pro Met Pro
1

<210> SEQ ID NO 20
<211> LENGTH: 3
<212> TYPE: PRT
<213> ORGANISM: Artificial Sequence
<220> FEATURE:
<223> OTHER INFORMATION: artificially synthesized sequence

<400> SEQUENCE: 20

Pro Met Pro
1

<210> SEQ ID NO 21
<211> LENGTH: 138
<212> TYPE: PRT
<213> ORGANISM: Artificial Sequence
<220> FEATURE:
<223> OTHER INFORMATION: artificially synthesized sequence
```

<400> SEQUENCE: 21

Tyr Pro His Pro Ala Tyr Pro Met Pro Phe Ile Thr Thr Ile Leu Gly
1               5                   10                  15

Gly Leu Tyr Pro Ser Lys Ser Ile Leu Leu Ser Gly Thr Val Leu Pro
            20                  25                  30

Ser Ala Gln Arg Phe His Ile Asn Leu Cys Ser Gly Asn His Ile Ala
        35                  40                  45

Phe His Leu Asn Pro Arg Phe Asp Glu Asn Ala Val Val Arg Asn Thr
    50                  55                  60

Gln Ile Asp Asn Ser Trp Gly Ser Glu Glu Arg Ser Leu Pro Arg Lys
65                  70                  75                  80

Met Pro Phe Val Arg Gly Gln Ser Phe Ser Val Trp Ile Leu Cys Glu
                85                  90                  95

Ala His Cys Leu Lys Val Ala Val Asp Gly Gln His Leu Phe Glu Tyr
            100                 105                 110

Tyr His Arg Leu Arg Asn Leu Pro Thr Ile Asn Arg Leu Glu Val Gly
        115                 120                 125

Gly Asp Ile Gln Leu Thr His Val Gln Thr
    130                 135

<210> SEQ ID NO 22
<211> LENGTH: 137
<212> TYPE: PRT
<213> ORGANISM: Artificial Sequence
<220> FEATURE:
<223> OTHER INFORMATION: artificially synthesized sequence

<400> SEQUENCE: 22

Pro His Pro Ala Tyr Pro Met Pro Phe Ile Thr Thr Ile Leu Gly Gly
1               5                   10                  15

Leu Tyr Pro Ser Lys Ser Ile Leu Leu Ser Gly Thr Val Leu Pro Ser
            20                  25                  30

Ala Gln Arg Phe His Ile Asn Leu Cys Ser Gly Asn His Ile Ala Phe
        35                  40                  45

His Leu Asn Pro Arg Phe Asp Glu Asn Ala Val Val Arg Asn Thr Gln
    50                  55                  60

Ile Asp Asn Ser Trp Gly Ser Glu Glu Arg Ser Leu Pro Arg Lys Met
65                  70                  75                  80

Pro Phe Val Arg Gly Gln Ser Phe Ser Val Trp Ile Leu Cys Glu Ala
                85                  90                  95

His Cys Leu Lys Val Ala Val Asp Gly Gln His Leu Phe Glu Tyr Tyr
            100                 105                 110

His Arg Leu Arg Asn Leu Pro Thr Ile Asn Arg Leu Glu Val Gly Gly
        115                 120                 125

Asp Ile Gln Leu Thr His Val Gln Thr
    130                 135

<210> SEQ ID NO 23
<211> LENGTH: 137
<212> TYPE: PRT
<213> ORGANISM: Artificial Sequence
<220> FEATURE:
<223> OTHER INFORMATION: artificially synthesized sequence

<400> SEQUENCE: 23

His Pro Pro Ala Tyr Pro Met Pro Phe Ile Thr Thr Ile Leu Gly Gly
1               5                   10                  15

Leu Tyr Pro Ser Lys Ser Ile Leu Leu Ser Gly Thr Val Leu Pro Ser
            20                  25                  30

Ala Gln Arg Phe His Ile Asn Leu Cys Ser Gly Asn His Ile Ala Phe
        35                  40                  45

His Leu Asn Pro Arg Phe Asp Glu Asn Ala Val Val Arg Asn Thr Gln
    50                  55                  60

Ile Asp Asn Ser Trp Gly Ser Glu Glu Arg Ser Leu Pro Arg Lys Met
65                  70                  75                  80

Pro Phe Val Arg Gly Gln Ser Phe Ser Val Trp Ile Leu Cys Glu Ala
                85                  90                  95

His Cys Leu Lys Val Ala Val Asp Gly Gln His Leu Phe Glu Tyr Tyr
            100                 105                 110

His Arg Leu Arg Asn Leu Pro Thr Ile Asn Arg Leu Glu Val Gly Gly
        115                 120                 125

Asp Ile Gln Leu Thr His Val Gln Thr
    130                 135

<210> SEQ ID NO 24
<211> LENGTH: 136
<212> TYPE: PRT
<213> ORGANISM: Artificial Sequence
<220> FEATURE:
<223> OTHER INFORMATION: artificially synthesized sequence

<400> SEQUENCE: 24

His Pro Ala Tyr Pro Met Pro Phe Ile Thr Thr Ile Leu Gly Gly Leu
1               5                   10                  15

Tyr Pro Ser Lys Ser Ile Leu Leu Ser Gly Thr Val Leu Pro Ser Ala
            20                  25                  30

Gln Arg Phe His Ile Asn Leu Cys Ser Gly Asn His Ile Ala Phe His
        35                  40                  45

Leu Asn Pro Arg Phe Asp Glu Asn Ala Val Val Arg Asn Thr Gln Ile
    50                  55                  60

Asp Asn Ser Trp Gly Ser Glu Glu Arg Ser Leu Pro Arg Lys Met Pro
65                  70                  75                  80

Phe Val Arg Gly Gln Ser Phe Ser Val Trp Ile Leu Cys Glu Ala His
                85                  90                  95

Cys Leu Lys Val Ala Val Asp Gly Gln His Leu Phe Glu Tyr Tyr His
            100                 105                 110

Arg Leu Arg Asn Leu Pro Thr Ile Asn Arg Leu Glu Val Gly Gly Asp
        115                 120                 125

Ile Gln Leu Thr His Val Gln Thr
    130                 135

<210> SEQ ID NO 25
<211> LENGTH: 136
<212> TYPE: PRT
<213> ORGANISM: Artificial Sequence
<220> FEATURE:
<223> OTHER INFORMATION: artificially synthesized sequence

<400> SEQUENCE: 25

His Ala Ala Tyr Pro Met Pro Phe Ile Thr Thr Ile Leu Gly Gly Leu
1               5                   10                  15

Tyr Pro Ser Lys Ser Ile Leu Leu Ser Gly Thr Val Leu Pro Ser Ala
            20                  25                  30

Gln Arg Phe His Ile Asn Leu Cys Ser Gly Asn His Ile Ala Phe His
        35                  40                  45

Leu Asn Pro Arg Phe Asp Glu Asn Ala Val Val Arg Asn Thr Gln Ile
    50                  55                  60

Asp Asn Ser Trp Gly Ser Glu Glu Arg Ser Leu Pro Arg Lys Met Pro
65                  70                  75                  80

Phe Val Arg Gly Gln Ser Phe Ser Val Trp Ile Leu Cys Glu Ala His
                85                  90                  95

Cys Leu Lys Val Ala Val Asp Gly Gln His Leu Phe Glu Tyr Tyr His
            100                 105                 110

Arg Leu Arg Asn Leu Pro Thr Ile Asn Arg Leu Glu Val Gly Gly Asp
        115                 120                 125

Ile Gln Leu Thr His Val Gln Thr
    130                 135

<210> SEQ ID NO 26
<211> LENGTH: 136
<212> TYPE: PRT
<213> ORGANISM: Artificial Sequence
<220> FEATURE:
<223> OTHER INFORMATION: artificially synthesized sequence

<400> SEQUENCE: 26

His Pro Ala Tyr Ala Met Pro Phe Ile Thr Thr Ile Leu Gly Gly Leu
1               5                   10                  15

Tyr Pro Ser Lys Ser Ile Leu Leu Ser Gly Thr Val Leu Pro Ser Ala
            20                  25                  30

Gln Arg Phe His Ile Asn Leu Cys Ser Gly Asn His Ile Ala Phe His
        35                  40                  45

Leu Asn Pro Arg Phe Asp Glu Asn Ala Val Val Arg Asn Thr Gln Ile
    50                  55                  60

Asp Asn Ser Trp Gly Ser Glu Glu Arg Ser Leu Pro Arg Lys Met Pro
65                  70                  75                  80

Phe Val Arg Gly Gln Ser Phe Ser Val Trp Ile Leu Cys Glu Ala His
                85                  90                  95

Cys Leu Lys Val Ala Val Asp Gly Gln His Leu Phe Glu Tyr Tyr His
            100                 105                 110

Arg Leu Arg Asn Leu Pro Thr Ile Asn Arg Leu Glu Val Gly Gly Asp
        115                 120                 125

Ile Gln Leu Thr His Val Gln Thr
    130                 135

<210> SEQ ID NO 27
<211> LENGTH: 136
<212> TYPE: PRT
<213> ORGANISM: Artificial Sequence
<220> FEATURE:
<223> OTHER INFORMATION: artificially synthesized sequence

<400> SEQUENCE: 27

His Pro Ala Pro Met Pro Phe Ile Thr Thr Ile Leu Gly Gly Leu
1               5                   10                  15

Tyr Pro Ser Lys Ser Ile Leu Leu Ser Gly Thr Val Leu Pro Ser Ala
            20                  25                  30

Gln Arg Phe His Ile Asn Leu Cys Ser Gly Asn His Ile Ala Phe His
        35                  40                  45

Leu Asn Pro Arg Phe Asp Glu Asn Ala Val Val Arg Asn Thr Gln Ile
    50                  55                  60

Asp Asn Ser Trp Gly Ser Glu Glu Arg Ser Leu Pro Arg Lys Met Pro
65                  70                  75                  80

Phe Val Arg Gly Gln Ser Phe Ser Val Trp Ile Leu Cys Glu Ala His
                85                  90                  95

Cys Leu Lys Val Ala Val Asp Gly Gln His Leu Phe Glu Tyr Tyr His
            100                 105                 110

Arg Leu Arg Asn Leu Pro Thr Ile Asn Arg Leu Glu Val Gly Gly Asp
        115                 120                 125

Ile Gln Leu Thr His Val Gln Thr
        130                 135

<210> SEQ ID NO 28
<211> LENGTH: 136
<212> TYPE: PRT
<213> ORGANISM: Artificial Sequence
<220> FEATURE:
<223> OTHER INFORMATION: artificially synthesized sequence

<400> SEQUENCE: 28

His Pro Pro Tyr Pro Met Pro Phe Ile Thr Thr Ile Leu Gly Gly Leu
1               5                   10                  15

Tyr Pro Ser Lys Ser Ile Leu Leu Ser Gly Thr Val Leu Pro Ser Ala
            20                  25                  30

Gln Arg Phe His Ile Asn Leu Cys Ser Gly Asn His Ile Ala Phe His
        35                  40                  45

Leu Asn Pro Arg Phe Asp Glu Asn Ala Val Val Arg Asn Thr Gln Ile
    50                  55                  60

Asp Asn Ser Trp Gly Ser Glu Glu Arg Ser Leu Pro Arg Lys Met Pro
65                  70                  75                  80

Phe Val Arg Gly Gln Ser Phe Ser Val Trp Ile Leu Cys Glu Ala His
                85                  90                  95

Cys Leu Lys Val Ala Val Asp Gly Gln His Leu Phe Glu Tyr Tyr His
            100                 105                 110

Arg Leu Arg Asn Leu Pro Thr Ile Asn Arg Leu Glu Val Gly Gly Asp
        115                 120                 125

Ile Gln Leu Thr His Val Gln Thr
        130                 135

<210> SEQ ID NO 29
<211> LENGTH: 135
<212> TYPE: PRT
<213> ORGANISM: Artificial Sequence
<220> FEATURE:
<223> OTHER INFORMATION: artificially synthesized sequence

<400> SEQUENCE: 29

Pro Ala Tyr Pro Met Pro Phe Ile Thr Thr Ile Leu Gly Gly Leu Tyr
1               5                   10                  15

Pro Ser Lys Ser Ile Leu Leu Ser Gly Thr Val Leu Pro Ser Ala Gln
            20                  25                  30

Arg Phe His Ile Asn Leu Cys Ser Gly Asn His Ile Ala Phe His Leu
        35                  40                  45

Asn Pro Arg Phe Asp Glu Asn Ala Val Val Arg Asn Thr Gln Ile Asp
    50                  55                  60

Asn Ser Trp Gly Ser Glu Glu Arg Ser Leu Pro Arg Lys Met Pro Phe
65                  70                  75                  80

Val Arg Gly Gln Ser Phe Ser Val Trp Ile Leu Cys Glu Ala His Cys
                85                  90                  95

Leu Lys Val Ala Val Asp Gly Gln His Leu Phe Glu Tyr Tyr His Arg
            100                 105                 110

Leu Arg Asn Leu Pro Thr Ile Asn Arg Leu Glu Val Gly Gly Asp Ile
        115                 120                 125

Gln Leu Thr His Val Gln Thr
    130                 135

<210> SEQ ID NO 30
<211> LENGTH: 135
<212> TYPE: PRT
<213> ORGANISM: Artificial Sequence
<220> FEATURE:
<223> OTHER INFORMATION: artificially synthesized sequence

<400> SEQUENCE: 30

Ala Pro Tyr Pro Met Pro Phe Ile Thr Thr Ile Leu Gly Gly Leu Tyr
1               5                   10                  15

Pro Ser Lys Ser Ile Leu Leu Ser Gly Thr Val Leu Pro Ser Ala Gln
            20                  25                  30

Arg Phe His Ile Asn Leu Cys Ser Gly Asn His Ile Ala Phe His Leu
        35                  40                  45

Asn Pro Arg Phe Asp Glu Asn Ala Val Val Arg Asn Thr Gln Ile Asp
    50                  55                  60

Asn Ser Trp Gly Ser Glu Glu Arg Ser Leu Pro Arg Lys Met Pro Phe
65                  70                  75                  80

Val Arg Gly Gln Ser Phe Ser Val Trp Ile Leu Cys Glu Ala His Cys
                85                  90                  95

Leu Lys Val Ala Val Asp Gly Gln His Leu Phe Glu Tyr Tyr His Arg
            100                 105                 110

Leu Arg Asn Leu Pro Thr Ile Asn Arg Leu Glu Val Gly Gly Asp Ile
        115                 120                 125

Gln Leu Thr His Val Gln Thr
    130                 135

<210> SEQ ID NO 31
<211> LENGTH: 135
<212> TYPE: PRT
<213> ORGANISM: Artificial Sequence
<220> FEATURE:
<223> OTHER INFORMATION: artificially synthesized sequence

<400> SEQUENCE: 31

Pro Pro Tyr Pro Met Pro Phe Ile Thr Thr Ile Leu Gly Gly Leu Tyr
1               5                   10                  15

Pro Ser Lys Ser Ile Leu Leu Ser Gly Thr Val Leu Pro Ser Ala Gln
            20                  25                  30

Arg Phe His Ile Asn Leu Cys Ser Gly Asn His Ile Ala Phe His Leu
        35                  40                  45

Asn Pro Arg Phe Asp Glu Asn Ala Val Val Arg Asn Thr Gln Ile Asp
    50                  55                  60

Asn Ser Trp Gly Ser Glu Glu Arg Ser Leu Pro Arg Lys Met Pro Phe
65                  70                  75                  80

Val Arg Gly Gln Ser Phe Ser Val Trp Ile Leu Cys Glu Ala His Cys
                85                  90                  95

Leu Lys Val Ala Val Asp Gly Gln His Leu Phe Glu Tyr Tyr His Arg
            100                 105                 110

Leu Arg Asn Leu Pro Thr Ile Asn Arg Leu Glu Val Gly Gly Asp Ile
        115                 120                 125

Gln Leu Thr His Val Gln Thr
    130                 135

<210> SEQ ID NO 32
<211> LENGTH: 134
<212> TYPE: PRT
<213> ORGANISM: Artificial Sequence
<220> FEATURE:
<223> OTHER INFORMATION: artificially synthesized sequence

<400> SEQUENCE: 32

Ala Tyr Pro Met Pro Phe Ile Thr Thr Ile Leu Gly Gly Leu Tyr Pro
1               5                   10                  15

Ser Lys Ser Ile Leu Leu Ser Gly Thr Val Leu Pro Ser Ala Gln Arg
            20                  25                  30

Phe His Ile Asn Leu Cys Ser Gly Asn His Ile Ala Phe His Leu Asn
        35                  40                  45

Pro Arg Phe Asp Glu Asn Ala Val Val Arg Asn Thr Gln Ile Asp Asn
    50                  55                  60

Ser Trp Gly Ser Glu Glu Arg Ser Leu Pro Arg Lys Met Pro Phe Val
65                  70                  75                  80

Arg Gly Gln Ser Phe Ser Val Trp Ile Leu Cys Glu Ala His Cys Leu
                85                  90                  95

Lys Val Ala Val Asp Gly Gln His Leu Phe Glu Tyr Tyr His Arg Leu
            100                 105                 110

Arg Asn Leu Pro Thr Ile Asn Arg Leu Glu Val Gly Gly Asp Ile Gln
        115                 120                 125

Leu Thr His Val Gln Thr
    130

<210> SEQ ID NO 33
<211> LENGTH: 133
<212> TYPE: PRT
<213> ORGANISM: Artificial Sequence
<220> FEATURE:
<223> OTHER INFORMATION: artificially synthesized sequence

<400> SEQUENCE: 33

Tyr Pro Met Pro Phe Ile Thr Thr Ile Leu Gly Gly Leu Tyr Pro Ser
1               5                   10                  15

Lys Ser Ile Leu Leu Ser Gly Thr Val Leu Pro Ser Ala Gln Arg Phe
            20                  25                  30

His Ile Asn Leu Cys Ser Gly Asn His Ile Ala Phe His Leu Asn Pro
        35                  40                  45

Arg Phe Asp Glu Asn Ala Val Val Arg Asn Thr Gln Ile Asp Asn Ser
    50                  55                  60

Trp Gly Ser Glu Glu Arg Ser Leu Pro Arg Lys Met Pro Phe Val Arg
65                  70                  75                  80

Gly Gln Ser Phe Ser Val Trp Ile Leu Cys Glu Ala His Cys Leu Lys
                85                  90                  95

Val Ala Val Asp Gly Gln His Leu Phe Glu Tyr Tyr His Arg Leu Arg
            100                 105                 110

Asn Leu Pro Thr Ile Asn Arg Leu Glu Val Gly Gly Asp Ile Gln Leu
        115                 120                 125

Thr His Val Gln Thr
    130

<210> SEQ ID NO 34
<211> LENGTH: 132
<212> TYPE: PRT
<213> ORGANISM: Artificial Sequence
<220> FEATURE:
<223> OTHER INFORMATION: artificially synthesized sequence

<400> SEQUENCE: 34

Pro Met Pro Phe Ile Thr Thr Ile Leu Gly Gly Leu Tyr Pro Ser Lys
1               5                   10                  15

Ser Ile Leu Leu Ser Gly Thr Val Leu Pro Ser Ala Gln Arg Phe His
            20                  25                  30

Ile Asn Leu Cys Ser Gly Asn His Ile Ala Phe His Leu Asn Pro Arg
        35                  40                  45

Phe Asp Glu Asn Ala Val Val Arg Asn Thr Gln Ile Asp Asn Ser Trp
    50                  55                  60

Gly Ser Glu Glu Arg Ser Leu Pro Arg Lys Met Pro Phe Val Arg Gly
65                  70                  75                  80

Gln Ser Phe Ser Val Trp Ile Leu Cys Glu Ala His Cys Leu Lys Val
                85                  90                  95

Ala Val Asp Gly Gln His Leu Phe Glu Tyr Tyr His Arg Leu Arg Asn
            100                 105                 110

Leu Pro Thr Ile Asn Arg Leu Glu Val Gly Gly Asp Ile Gln Leu Thr
        115                 120                 125

His Val Gln Thr
    130

<210> SEQ ID NO 35
<211> LENGTH: 286
<212> TYPE: PRT
<213> ORGANISM: Artificial Sequence
<220> FEATURE:
<223> OTHER INFORMATION: artificially synthesized sequence -continued

```
<400> SEQUENCE: 35

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Tyr Pro His Pro Ala Tyr Pro Met Pro Phe Ile Thr
145                 150                 155                 160

Thr Ile Leu Gly Gly Leu Tyr Pro Ser Lys Ser Ile Leu Leu Ser Gly
                165                 170                 175

Thr Val Leu Pro Ser Ala Gln Arg Phe His Ile Asn Leu Cys Ser Gly
            180                 185                 190

Asn His Ile Ala Phe His Leu Asn Pro Arg Phe Asp Glu Asn Ala Val
        195                 200                 205

Val Arg Asn Thr Gln Ile Asp Asn Ser Trp Gly Ser Glu Glu Arg Ser
    210                 215                 220

Leu Pro Arg Lys Met Pro Phe Val Arg Gly Gln Ser Phe Ser Val Trp
225                 230                 235                 240

Ile Leu Cys Glu Ala His Cys Leu Lys Val Ala Val Asp Gly Gln His
                245                 250                 255

Leu Phe Glu Tyr Tyr His Arg Leu Arg Asn Leu Pro Thr Ile Asn Arg
            260                 265                 270

Leu Glu Val Gly Gly Asp Ile Gln Leu Thr His Val Gln Thr
        275                 280                 285

<210> SEQ ID NO 36
<211> LENGTH: 285
<212> TYPE: PRT
<213> ORGANISM: Artificial Sequence
<220> FEATURE:
<223> OTHER INFORMATION: artificially synthesized sequence

<400> SEQUENCE: 36

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60
```

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
            85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
            130                 135                 140

Ile Ser Phe Gln Pro His Pro Ala Tyr Pro Met Pro Phe Ile Thr Thr
145                 150                 155                 160

Ile Leu Gly Gly Leu Tyr Pro Ser Lys Ser Ile Leu Leu Ser Gly Thr
            165                 170                 175

Val Leu Pro Ser Ala Gln Arg Phe His Ile Asn Leu Cys Ser Gly Asn
            180                 185                 190

His Ile Ala Phe His Leu Asn Pro Arg Phe Asp Glu Asn Ala Val Val
            195                 200                 205

Arg Asn Thr Gln Ile Asp Asn Ser Trp Gly Ser Glu Glu Arg Ser Leu
210                 215                 220

Pro Arg Lys Met Pro Phe Val Arg Gly Gln Ser Phe Ser Val Trp Ile
225                 230                 235                 240

Leu Cys Glu Ala His Cys Leu Lys Val Ala Val Asp Gly Gln His Leu
            245                 250                 255

Phe Glu Tyr Tyr His Arg Leu Arg Asn Leu Pro Thr Ile Asn Arg Leu
            260                 265                 270

Glu Val Gly Gly Asp Ile Gln Leu Thr His Val Gln Thr
            275                 280                 285

<210> SEQ ID NO 37
<211> LENGTH: 285
<212> TYPE: PRT
<213> ORGANISM: Artificial Sequence
<220> FEATURE:
<223> OTHER INFORMATION: artificially synthesized sequence

<400> SEQUENCE: 37

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
            35                  40                  45

Phe Gln Thr Gly Phe Ser Gly Asn Asp Ile Ala Phe His Phe Asn Pro
50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
            85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
            130                 135                 140

Ile Ser Phe Gln His Pro Ala Tyr Pro Met Pro Phe Ile Thr Thr
145                 150                 155                 160

Ile Leu Gly Gly Leu Tyr Pro Ser Lys Ser Ile Leu Leu Ser Gly Thr
                165                 170                 175

Val Leu Pro Ser Ala Gln Arg Phe His Ile Asn Leu Cys Ser Gly Asn
            180                 185                 190

His Ile Ala Phe His Leu Asn Pro Arg Phe Asp Glu Asn Ala Val Val
            195                 200                 205

Arg Asn Thr Gln Ile Asp Asn Ser Trp Gly Ser Glu Glu Arg Ser Leu
        210                 215                 220

Pro Arg Lys Met Pro Phe Val Arg Gly Gln Ser Phe Ser Val Trp Ile
225                 230                 235                 240

Leu Cys Glu Ala His Cys Leu Lys Val Ala Val Asp Gly Gln His Leu
                245                 250                 255

Phe Glu Tyr Tyr His Arg Leu Arg Asn Leu Pro Thr Ile Asn Arg Leu
            260                 265                 270

Glu Val Gly Gly Asp Ile Gln Leu Thr His Val Gln Thr
275                 280                 285

<210> SEQ ID NO 38
<211> LENGTH: 284
<212> TYPE: PRT
<213> ORGANISM: Artificial Sequence
<220> FEATURE:
<223> OTHER INFORMATION: artificially synthesized sequence

<400> SEQUENCE: 38

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
                20                  25                  30

Val Asn Gly Thr Val Leu Ser Ser Gly Thr Arg Phe Ala Val Asn
            35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
                100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
        130                 135                 140

Ile Ser Phe Gln His Pro Ala Tyr Pro Met Pro Phe Ile Thr Thr Ile
145                 150                 155                 160

Leu Gly Gly Leu Tyr Pro Ser Lys Ser Ile Leu Leu Ser Gly Thr Val
                165                 170                 175

Leu Pro Ser Ala Gln Arg Phe His Ile Asn Leu Cys Ser Gly Asn His
            180                 185                 190

Ile Ala Phe His Leu Asn Pro Arg Phe Asp Glu Asn Ala Val Val Arg
        195                 200                 205

Asn Thr Gln Ile Asp Asn Ser Trp Gly Ser Glu Glu Arg Ser Leu Pro
    210                 215                 220

Arg Lys Met Pro Phe Val Arg Gly Gln Ser Phe Ser Val Trp Ile Leu
225                 230                 235                 240

Cys Glu Ala His Cys Leu Lys Val Ala Val Asp Gly Gln His Leu Phe
                245                 250                 255

Glu Tyr Tyr His Arg Leu Arg Asn Leu Pro Thr Ile Asn Arg Leu Glu
            260                 265                 270

Val Gly Gly Asp Ile Gln Leu Thr His Val Gln Thr
        275                 280

<210> SEQ ID NO 39
<211> LENGTH: 284
<212> TYPE: PRT
<213> ORGANISM: Artificial Sequence
<220> FEATURE:
<223> OTHER INFORMATION: artificially synthesized sequence

<400> SEQUENCE: 39

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln His Ala Ala Tyr Pro Met Pro Phe Ile Thr Thr Ile
145                 150                 155                 160

Leu Gly Gly Leu Tyr Pro Ser Lys Ser Ile Leu Leu Ser Gly Thr Val
                165                 170                 175

Leu Pro Ser Ala Gln Arg Phe His Ile Asn Leu Cys Ser Gly Asn His
            180                 185                 190

Ile Ala Phe His Leu Asn Pro Arg Phe Asp Glu Asn Ala Val Val Arg
        195                 200                 205

Asn Thr Gln Ile Asp Asn Ser Trp Gly Ser Glu Glu Arg Ser Leu Pro
    210                 215                 220

Arg Lys Met Pro Phe Val Arg Gly Gln Ser Phe Ser Val Trp Ile Leu
225                 230                 235                 240

Cys Glu Ala His Cys Leu Lys Val Ala Val Asp Gly Gln His Leu Phe
                245                 250                 255

Glu Tyr Tyr His Arg Leu Arg Asn Leu Pro Thr Ile Asn Arg Leu Glu
            260                 265                 270

Val Gly Gly Asp Ile Gln Leu Thr His Val Gln Thr
        275                 280

```
<210> SEQ ID NO 40
<211> LENGTH: 284
<212> TYPE: PRT
<213> ORGANISM: Artificial Sequence
<220> FEATURE:
<223> OTHER INFORMATION: artificially synthesized sequence

<400> SEQUENCE: 40

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln His Pro Ala Tyr Ala Met Pro Phe Ile Thr Thr Ile
145                 150                 155                 160

Leu Gly Gly Leu Tyr Pro Ser Lys Ser Ile Leu Leu Ser Gly Thr Val
                165                 170                 175

Leu Pro Ser Ala Gln Arg Phe His Ile Asn Leu Cys Ser Gly Asn His
            180                 185                 190

Ile Ala Phe His Leu Asn Pro Arg Phe Asp Glu Asn Ala Val Val Arg
        195                 200                 205

Asn Thr Gln Ile Asp Asn Ser Trp Gly Ser Glu Glu Arg Ser Leu Pro
    210                 215                 220

Arg Lys Met Pro Phe Val Arg Gly Gln Ser Phe Ser Val Trp Ile Leu
225                 230                 235                 240

Cys Glu Ala His Cys Leu Lys Val Ala Val Asp Gly Gln His Leu Phe
                245                 250                 255

Glu Tyr Tyr His Arg Leu Arg Asn Leu Pro Thr Ile Asn Arg Leu Glu
            260                 265                 270

Val Gly Gly Asp Ile Gln Leu Thr His Val Gln Thr
        275                 280

<210> SEQ ID NO 41
<211> LENGTH: 284
<212> TYPE: PRT
<213> ORGANISM: Artificial Sequence
<220> FEATURE:
<223> OTHER INFORMATION: artificially synthesized sequence

<400> SEQUENCE: 41

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30
```

Val Asn Gly Thr Val Leu Ser Ser Gly Thr Arg Phe Ala Val Asn
          35                  40                  45

Phe Gln Thr Gly Phe Ser Gly Asn Asp Ile Ala Phe His Phe Asn Pro
 50                      55                  60

Arg Phe Glu Asp Gly Gly Tyr Val Val Cys Asn Thr Arg Gln Asn Gly
 65                  70                  75                  80

Ser Trp Gly Pro Glu Glu Arg Lys Thr His Met Pro Phe Gln Lys Gly
                     85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
            130                 135                 140

Ile Ser Phe Gln His Pro Ala Pro Met Pro Phe Ile Thr Thr Ile
145                 150                 155                 160

Leu Gly Gly Leu Tyr Pro Ser Lys Ser Ile Leu Leu Ser Gly Thr Val
                    165                 170                 175

Leu Pro Ser Ala Gln Arg Phe His Ile Asn Leu Cys Ser Gly Asn His
            180                 185                 190

Ile Ala Phe His Leu Asn Pro Arg Phe Asp Glu Asn Ala Val Val Arg
            195                 200                 205

Asn Thr Gln Ile Asp Asn Ser Trp Gly Ser Glu Glu Arg Ser Leu Pro
            210                 215                 220

Arg Lys Met Pro Phe Val Arg Gly Gln Ser Phe Ser Val Trp Ile Leu
225                 230                 235                 240

Cys Glu Ala His Cys Leu Lys Val Ala Val Asp Gly Gln His Leu Phe
                    245                 250                 255

Glu Tyr Tyr His Arg Leu Arg Asn Leu Pro Thr Ile Asn Arg Leu Glu
            260                 265                 270

Val Gly Gly Asp Ile Gln Leu Thr His Val Gln Thr
            275                 280

<210> SEQ ID NO 42
<211> LENGTH: 284
<212> TYPE: PRT
<213> ORGANISM: Artificial Sequence
<220> FEATURE:
<223> OTHER INFORMATION: artificially synthesized sequence

<400> SEQUENCE: 42

Met Ala Phe Ser Gly Ser Gln Ala Pro Tyr Leu Ser Pro Ala Val Pro
 1               5                  10                  15

Phe Ser Gly Thr Ile Gln Gly Gly Leu Gln Asp Gly Leu Gln Ile Thr
                20                  25                  30

Val Asn Gly Thr Val Leu Ser Ser Ser Gly Thr Arg Phe Ala Val Asn
            35                  40                  45

Phe Gln Thr Gly Phe Ser Gly Asn Asp Ile Ala Phe His Phe Asn Pro
 50                      55                  60

Arg Phe Glu Asp Gly Gly Tyr Val Val Cys Asn Thr Arg Gln Asn Gly
 65                  70                  75                  80

Ser Trp Gly Pro Glu Glu Arg Lys Thr His Met Pro Phe Gln Lys Gly
                     85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
            130                 135                 140

Ile Ser Phe Gln His Pro Pro Tyr Pro Met Pro Phe Ile Thr Thr Ile
145                 150                 155                 160

Leu Gly Gly Leu Tyr Pro Ser Lys Ser Ile Leu Leu Ser Gly Thr Val
                165                 170                 175

Leu Pro Ser Ala Gln Arg Phe His Ile Asn Leu Cys Ser Gly Asn His
            180                 185                 190

Ile Ala Phe His Leu Asn Pro Arg Phe Asp Glu Asn Ala Val Val Arg
            195                 200                 205

Asn Thr Gln Ile Asp Asn Ser Trp Gly Ser Glu Glu Arg Ser Leu Pro
            210                 215                 220

Arg Lys Met Pro Phe Val Arg Gly Gln Ser Phe Ser Val Trp Ile Leu
225                 230                 235                 240

Cys Glu Ala His Cys Leu Lys Val Ala Val Asp Gly Gln His Leu Phe
                245                 250                 255

Glu Tyr Tyr His Arg Leu Arg Asn Leu Pro Thr Ile Asn Arg Leu Glu
            260                 265                 270

Val Gly Gly Asp Ile Gln Leu Thr His Val Gln Thr
            275                 280

<210> SEQ ID NO 43
<211> LENGTH: 283
<212> TYPE: PRT
<213> ORGANISM: Artificial Sequence
<220> FEATURE:
<223> OTHER INFORMATION: artificially synthesized sequence

<400> SEQUENCE: 43

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
                20                  25                  30

Val Asn Gly Thr Val Leu Ser Ser Gly Thr Arg Phe Ala Val Asn
            35                  40                  45

Phe Gln Thr Gly Phe Ser Gly Asn Asp Ile Ala Phe His Phe Asn Pro
            50                  55                  60

Arg Phe Glu Asp Gly Gly Tyr Val Val Cys Asn Thr Arg Gln Asn Gly
65              70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
            130                 135                 140

Ile Ser Phe Gln Pro Ala Tyr Pro Met Pro Phe Ile Thr Thr Ile Leu
145                 150                 155                 160

Gly Gly Leu Tyr Pro Ser Lys Ser Ile Leu Leu Ser Gly Thr Val Leu
                165                 170                 175

Pro Ser Ala Gln Arg Phe His Ile Asn Leu Cys Ser Gly Asn His Ile
            180                 185                 190

```
Ala Phe His Leu Asn Pro Arg Phe Asp Glu Asn Ala Val Val Arg Asn
            195                 200                 205

Thr Gln Ile Asp Asn Ser Trp Gly Ser Glu Glu Arg Ser Leu Pro Arg
    210                 215                 220

Lys Met Pro Phe Val Arg Gly Gln Ser Phe Ser Val Trp Ile Leu Cys
225                 230                 235                 240

Glu Ala His Cys Leu Lys Val Ala Val Asp Gly Gln His Leu Phe Glu
            245                 250                 255

Tyr Tyr His Arg Leu Arg Asn Leu Pro Thr Ile Asn Arg Leu Glu Val
            260                 265                 270

Gly Gly Asp Ile Gln Leu Thr His Val Gln Thr
            275                 280
```

<210> SEQ ID NO 44
<211> LENGTH: 283
<212> TYPE: PRT
<213> ORGANISM: Artificial Sequence
<220> FEATURE:
<223> OTHER INFORMATION: artificially synthesized sequence

<400> SEQUENCE: 44

```
Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Ala Pro Tyr Pro Met Pro Phe Ile Thr Thr Ile Leu
145                 150                 155                 160

Gly Gly Leu Tyr Pro Ser Lys Ser Ile Leu Leu Ser Gly Thr Val Leu
                165                 170                 175

Pro Ser Ala Gln Arg Phe His Ile Asn Leu Cys Ser Gly Asn His Ile
            180                 185                 190

Ala Phe His Leu Asn Pro Arg Phe Asp Glu Asn Ala Val Val Arg Asn
        195                 200                 205

Thr Gln Ile Asp Asn Ser Trp Gly Ser Glu Glu Arg Ser Leu Pro Arg
    210                 215                 220

Lys Met Pro Phe Val Arg Gly Gln Ser Phe Ser Val Trp Ile Leu Cys
225                 230                 235                 240

Glu Ala His Cys Leu Lys Val Ala Val Asp Gly Gln His Leu Phe Glu
                245                 250                 255
```

Tyr Tyr His Arg Leu Arg Asn Leu Pro Thr Ile Asn Arg Leu Glu Val
            260                 265                 270

Gly Gly Asp Ile Gln Leu Thr His Val Gln Thr
        275                 280

<210> SEQ ID NO 45
<211> LENGTH: 283
<212> TYPE: PRT
<213> ORGANISM: Artificial Sequence
<220> FEATURE:
<223> OTHER INFORMATION: artificially synthesized sequence

<400> SEQUENCE: 45

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Val Asn Gly Thr Val Leu Ser Ser Gly Thr Arg Phe Ala Val Asn
            85                  90                  95

Met Pro Phe Asp Leu Cys Phe Leu Val Gln Ser Ser Asp Phe Lys Val
                100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
        130                 135                 140

Ile Ser Phe Gln Pro Pro Tyr Pro Met Pro Phe Ile Thr Thr Ile Leu
145                 150                 155                 160

Gly Gly Leu Tyr Pro Ser Lys Ser Ile Leu Leu Ser Gly Thr Val Leu
                165                 170                 175

Pro Ser Ala Gln Arg Phe His Ile Asn Leu Cys Ser Gly Asn His Ile
            180                 185                 190

Ala Phe His Leu Asn Pro Arg Phe Asp Glu Asn Ala Val Val Arg Asn
        195                 200                 205

Thr Gln Ile Asp Asn Ser Trp Gly Ser Glu Glu Arg Ser Leu Pro Arg
    210                 215                 220

Lys Met Pro Phe Val Arg Gly Gln Ser Phe Ser Val Trp Ile Leu Cys
225                 230                 235                 240

Glu Ala His Cys Leu Lys Val Ala Val Asp Gly Gln His Leu Phe Glu
                245                 250                 255

Tyr Tyr His Arg Leu Arg Asn Leu Pro Thr Ile Asn Arg Leu Glu Val
            260                 265                 270

Gly Gly Asp Ile Gln Leu Thr His Val Gln Thr
        275                 280

<210> SEQ ID NO 46
<211> LENGTH: 282
<212> TYPE: PRT
<213> ORGANISM: Artificial Sequence
<220> FEATURE:
<223> OTHER INFORMATION: artificially synthesized sequence -continued

```
<400> SEQUENCE: 46

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Ala Tyr Pro Met Pro Phe Ile Thr Thr Ile Leu Gly
145                 150                 155                 160

Gly Leu Tyr Pro Ser Lys Ser Ile Leu Leu Ser Gly Thr Val Leu Pro
                165                 170                 175

Ser Ala Gln Arg Phe His Ile Asn Leu Cys Ser Gly Asn His Ile Ala
            180                 185                 190

Phe His Leu Asn Pro Arg Phe Asp Glu Asn Ala Val Val Arg Asn Thr
        195                 200                 205

Gln Ile Asp Asn Ser Trp Gly Ser Glu Glu Arg Ser Leu Pro Arg Lys
    210                 215                 220

Met Pro Phe Val Arg Gly Gln Ser Phe Ser Val Trp Ile Leu Cys Glu
225                 230                 235                 240

Ala His Cys Leu Lys Val Ala Val Asp Gly Gln His Leu Phe Glu Tyr
                245                 250                 255

Tyr His Arg Leu Arg Asn Leu Pro Thr Ile Asn Arg Leu Glu Val Gly
            260                 265                 270

Gly Asp Ile Gln Leu Thr His Val Gln Thr
        275                 280

<210> SEQ ID NO 47
<211> LENGTH: 281
<212> TYPE: PRT
<213> ORGANISM: Artificial Sequence
<220> FEATURE:
<223> OTHER INFORMATION: artificially synthesized sequence

<400> SEQUENCE: 47

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60
```

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
            85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
            130                 135                 140

Ile Ser Phe Gln Tyr Pro Met Pro Phe Ile Thr Thr Ile Leu Gly Gly
145                 150                 155                 160

Leu Tyr Pro Ser Lys Ser Ile Leu Leu Ser Gly Thr Val Leu Pro Ser
                165                 170                 175

Ala Gln Arg Phe His Ile Asn Leu Cys Ser Gly Asn His Ile Ala Phe
            180                 185                 190

His Leu Asn Pro Arg Phe Asp Glu Asn Ala Val Val Arg Asn Thr Gln
            195                 200                 205

Ile Asp Asn Ser Trp Gly Ser Glu Glu Arg Ser Leu Pro Arg Lys Met
210                 215                 220

Pro Phe Val Arg Gly Gln Ser Phe Ser Val Trp Ile Leu Cys Glu Ala
225                 230                 235                 240

His Cys Leu Lys Val Ala Val Asp Gly Gln His Leu Phe Glu Tyr Tyr
                245                 250                 255

His Arg Leu Arg Asn Leu Pro Thr Ile Asn Arg Leu Glu Val Gly Gly
            260                 265                 270

Asp Ile Gln Leu Thr His Val Gln Thr
            275                 280

<210> SEQ ID NO 48
<211> LENGTH: 280
<212> TYPE: PRT
<213> ORGANISM: Artificial Sequence
<220> FEATURE:
<223> OTHER INFORMATION: artificially synthesized sequence

<400> SEQUENCE: 48

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
            35                  40                  45

Phe Gln Thr Gly Phe Ser Gly Asn Asp Ile Ala Phe His Phe Asn Pro
50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
            85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
            130                 135                 140

```
Ile Ser Phe Gln Pro Met Pro Phe Ile Thr Thr Ile Leu Gly Gly Leu
145                 150                 155                 160

Tyr Pro Ser Lys Ser Ile Leu Leu Ser Gly Thr Val Leu Pro Ser Ala
            165                 170                 175

Gln Arg Phe His Ile Asn Leu Cys Ser Gly Asn His Ile Ala Phe His
            180                 185                 190

Leu Asn Pro Arg Phe Asp Glu Asn Ala Val Val Arg Asn Thr Gln Ile
            195                 200                 205

Asp Asn Ser Trp Gly Ser Glu Glu Arg Ser Leu Pro Arg Lys Met Pro
210                 215                 220

Phe Val Arg Gly Gln Ser Phe Ser Val Trp Ile Leu Cys Glu Ala His
225                 230                 235                 240

Cys Leu Lys Val Ala Val Asp Gly Gln His Leu Phe Glu Tyr Tyr His
            245                 250                 255

Arg Leu Arg Asn Leu Pro Thr Ile Asn Arg Leu Glu Val Gly Gly Asp
            260                 265                 270

Ile Gln Leu Thr His Val Gln Thr
            275                 280

<210> SEQ ID NO 49
<211> LENGTH: 27
<212> TYPE: DNA
<213> ORGANISM: Artificial Sequence
<220> FEATURE:
<223> OTHER INFORMATION: artificially synthesized sequence

<400> SEQUENCE: 49 taccccacc ccgcctatcc gatgcct                                            27

<210> SEQ ID NO 50
<211> LENGTH: 24
<212> TYPE: DNA
<213> ORGANISM: Artificial Sequence
<220> FEATURE:
<223> OTHER INFORMATION: artificially synthesized sequence

<400> SEQUENCE: 50
ccccaccccg cctatccgat gcct                                              24

<210> SEQ ID NO 51
<211> LENGTH: 24
<212> TYPE: DNA
<213> ORGANISM: Artificial Sequence
<220> FEATURE:
<223> OTHER INFORMATION: artificially synthesized sequence

<400> SEQUENCE: 51
cacccgcccg cctatccgat gcct                                              24

<210> SEQ ID NO 52
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 52 cacccgcct atccgatgcc t                                                  21
```

```
<210> SEQ ID NO 53
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 53
cacgccgcct atccgatgcc t                                              21

<210> SEQ ID NO 54
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 54
caccccgcct atgcgatgcc t                                              21

<210> SEQ ID NO 55
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 55
caccccgccc cgccgatgcc t                                              21

<210> SEQ ID NO 56
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 56 cacccccct atccgatgcc t                                               21

<210> SEQ ID NO 57
<211> LENGTH: 18
<212> TYPE: DNA
<213> ORGANISM: Artificial Sequence
<220> FEATURE:
<223> OTHER INFORMATION: artificially synthesized sequence

<400> SEQUENCE: 57
cccgcctatc cgatgcct                                                  18

<210> SEQ ID NO 58
<211> LENGTH: 18
<212> TYPE: DNA
<213> ORGANISM: Artificial Sequence
<220> FEATURE:
<223> OTHER INFORMATION: artificially synthesized sequence

<400> SEQUENCE: 58
gccccctatc cgatgcct                                                  18

<210> SEQ ID NO 59
<211> LENGTH: 18
<212> TYPE: DNA
<213> ORGANISM: Artificial Sequence
<220> FEATURE:
<223> OTHER INFORMATION: artificially synthesized sequence
```

```
<400> SEQUENCE: 59
cccccctatc cgatgcct                                                     18

<210> SEQ ID NO 60
<211> LENGTH: 15
<212> TYPE: DNA
<213> ORGANISM: Artificial Sequence
<220> FEATURE:
<223> OTHER INFORMATION: artificially synthesized sequence

<400> SEQUENCE: 60
gcctatccga tgcct                                                        15

<210> SEQ ID NO 61
<211> LENGTH: 12
<212> TYPE: DNA
<213> ORGANISM: Artificial Sequence
<220> FEATURE:
<223> OTHER INFORMATION: artificially synthesized sequence

<400> SEQUENCE: 61
tatccgatgc ct                                                           12

<210> SEQ ID NO 62
<211> LENGTH: 9
<212> TYPE: DNA
<213> ORGANISM: Artificial Sequence
<220> FEATURE:
<223> OTHER INFORMATION: artificially synthesized sequence

<400> SEQUENCE: 62 ccgatgcct                                                                9

<210> SEQ ID NO 63
<211> LENGTH: 417
<212> TYPE: DNA
<213> ORGANISM: Artificial Sequence
<220> FEATURE:
<223> OTHER INFORMATION: artificially synthesized sequence

<400> SEQUENCE: 63
tacccccacc ccgcctatcc gatgcctttc atcaccacca ttctgggagg gctgtaccca        60
tccaagtcca tcctcctgtc aggcactgtc ctgcccagtg ctcagaggtt ccacatcaac       120
ctgtgctctg gaaccacat cgccttccac ctgaaccccc gttttgatga gaatgctgtg        180
gtccgcaaca cccagatcga caactcctgg gggtctgagg agcgaagtct gccccgaaaa       240
atgcccttcg tccgtggcca gagcttctca gtgtggatct tgtgtgaagc tcactgcctc      300
aaggtggccg tggatggtca gcacctgttt gaatactacc atcgcctgag gaacctgccc      360
accatcaaca gactggaagt ggggggcgac atccagctga cccatgtgca gacatag         417

<210> SEQ ID NO 64
<211> LENGTH: 414
<212> TYPE: DNA
<213> ORGANISM: Artificial Sequence
<220> FEATURE:
<223> OTHER INFORMATION: artificially synthesized sequence

<400> SEQUENCE: 64 ccccacccg cctatccgat gcctttcatc accaccattc tgggagggct gtacccatcc        60
aagtccatcc tcctgtcagg cactgtcctg cccagtgctg agaggttcca catcaacctg      120
tgctctggga accacatcgc cttccacctg aaccccgtt ttgatgagaa tgctgtggtc       180
```

| | |
|---|---|
| cgcaacaccc agatcgacaa ctcctggggg tctgaggagc gaagtctgcc ccgaaaaatg | 240 |
| cccttcgtcc gtggccagag cttctcagtg tggatcttgt gtgaagctca ctgcctcaag | 300 |
| gtggccgtgg atggtcagca cctgtttgaa tactaccatc gcctgaggaa cctgcccacc | 360 |
| atcaacagac tggaagtggg gggcgacatc cagctgaccc atgtgcagac atag | 414 |

<210> SEQ ID NO 65
<211> LENGTH: 414
<212> TYPE: DNA
<213> ORGANISM: Artificial Sequence
<220> FEATURE:
<223> OTHER INFORMATION: artificially synthesized sequence

<400> SEQUENCE: 65

| | |
|---|---|
| cacccgcccg cctatccgat gcctttcatc accaccattc tgggagggct gtacccatcc | 60 |
| aagtccatcc tcctgtcagg cactgtcctg cccagtgctc agaggttcca catcaacctg | 120 |
| tgctctggga accacatcgc cttccacctg aaccccgtt ttgatgagaa tgctgtggtc | 180 |
| cgcaacaccc agatcgacaa ctcctggggg tctgaggagc gaagtctgcc ccgaaaaatg | 240 |
| cccttcgtcc gtggccagag cttctcagtg tggatcttgt gtgaagctca ctgcctcaag | 300 |
| gtggccgtgg atggtcagca cctgtttgaa tactaccatc gcctgaggaa cctgcccacc | 360 |
| atcaacagac tggaagtggg gggcgacatc cagctgaccc atgtgcagac atag | 414 |

<210> SEQ ID NO 66
<211> LENGTH: 411
<212> TYPE: DNA
<213> ORGANISM: Artificial Sequence
<220> FEATURE:
<223> OTHER INFORMATION: artificially synthesized sequence

<400> SEQUENCE: 66

| | |
|---|---|
| caccccgcct atccgatgcc tttcatcacc accattctgg gagggctgta cccatccaag | 60 |
| tccatcctcc tgtcaggcac tgtcctgccc agtgctcaga ggttccacat caacctgtgc | 120 |
| tctgggaacc acatcgcctt ccacctgaac cccgttttg atgagaatgc tgtggtccgc | 180 |
| aacacccaga tcgacaactc tgggggtct gaggagcgaa gtctgccccg aaaaatgccc | 240 |
| ttcgtccgtg gccagagctt ctcagtgtgg atcttgtgtg aagctcactg cctcaaggtg | 300 |
| gccgtggatg gtcagcacct gtttgaatac taccatcgcc tgaggaacct gcccaccatc | 360 |
| aacagactgg aagtgggggg cgacatccag ctgacccatg tgcagacata g | 411 |

<210> SEQ ID NO 67
<211> LENGTH: 411
<212> TYPE: DNA
<213> ORGANISM: Artificial Sequence
<220> FEATURE:
<223> OTHER INFORMATION: artificially synthesized sequence

<400> SEQUENCE: 67

| | |
|---|---|
| cacgccgcct atccgatgcc tttcatcacc accattctgg gagggctgta cccatccaag | 60 |
| tccatcctcc tgtcaggcac tgtcctgccc agtgctcaga ggttccacat caacctgtgc | 120 |
| tctgggaacc acatcgcctt ccacctgaac cccgttttg atgagaatgc tgtggtccgc | 180 |
| aacacccaga tcgacaactc tgggggtct gaggagcgaa gtctgccccg aaaaatgccc | 240 |
| ttcgtccgtg gccagagctt ctcagtgtgg atcttgtgtg aagctcactg cctcaaggtg | 300 |
| gccgtggatg gtcagcacct gtttgaatac taccatcgcc tgaggaacct gcccaccatc | 360 |
| aacagactgg aagtgggggg cgacatccag ctgacccatg tgcagacata g | 411 |

```
<210> SEQ ID NO 68
<211> LENGTH: 411
<212> TYPE: DNA
<213> ORGANISM: Artificial Sequence
<220> FEATURE:
<223> OTHER INFORMATION: artificially synthesized sequence

<400> SEQUENCE: 68
caccccgcct atgcgatgcc tttcatcacc accattctgg gagggctgta cccatccaag      60
tccatcctcc tgtcaggcac tgtcctgccc agtgctcaga ggttccacat caacctgtgc     120
tctgggaacc acatcgcctt ccacctgaac ccccgttttg atgagaatgc tgtggtccgc     180
aacacccaga tcgacaactc ctgggggtct gaggagcgaa gtctgccccg aaaaatgccc     240
ttcgtccgtg gccagagctt ctcagtgtgg atcttgtgtg aagctcactg cctcaaggtg     300
gccgtggatg gtcagcacct gtttgaatac taccatcgcc tgaggaacct gcccaccatc     360
aacagactgg aagtgggggg cgacatccag ctgacccatg tgcagacata g              411

<210> SEQ ID NO 69
<211> LENGTH: 411
<212> TYPE: DNA
<213> ORGANISM: Artificial Sequence
<220> FEATURE:
<223> OTHER INFORMATION: artificially synthesized sequence

<400> SEQUENCE: 69
caccccgccc cgccgatgcc tttcatcacc accattctgg gagggctgta cccatccaag      60
tccatcctcc tgtcaggcac tgtcctgccc agtgctcaga ggttccacat caacctgtgc     120
tctgggaacc acatcgcctt ccacctgaac ccccgttttg atgagaatgc tgtggtccgc     180
aacacccaga tcgacaactc ctgggggtct gaggagcgaa gtctgccccg aaaaatgccc     240
ttcgtccgtg gccagagctt ctcagtgtgg atcttgtgtg aagctcactg cctcaaggtg     300
gccgtggatg gtcagcacct gtttgaatac taccatcgcc tgaggaacct gcccaccatc     360
aacagactgg aagtgggggg cgacatccag ctgacccatg tgcagacata g              411

<210> SEQ ID NO 70
<211> LENGTH: 411
<212> TYPE: DNA
<213> ORGANISM: Artificial Sequence
<220> FEATURE:
<223> OTHER INFORMATION: artificially synthesized sequence

<400> SEQUENCE: 70
caccccccct atccgatgcc tttcatcacc accattctgg gagggctgta cccatccaag      60
tccatcctcc tgtcaggcac tgtcctgccc agtgctcaga ggttccacat caacctgtgc     120
tctgggaacc acatcgcctt ccacctgaac ccccgttttg atgagaatgc tgtggtccgc     180
aacacccaga tcgacaactc ctgggggtct gaggagcgaa gtctgccccg aaaaatgccc     240
ttcgtccgtg gccagagctt ctcagtgtgg atcttgtgtg aagctcactg cctcaaggtg     300
gccgtggatg gtcagcacct gtttgaatac taccatcgcc tgaggaacct gcccaccatc     360
aacagactgg aagtgggggg cgacatccag ctgacccatg tgcagacata g              411

<210> SEQ ID NO 71
<211> LENGTH: 408
<212> TYPE: DNA
<213> ORGANISM: Artificial Sequence
<220> FEATURE:
<223> OTHER INFORMATION: artificially synthesized sequence
```

<400> SEQUENCE: 71

```
cccgcctatc cgatgccttt catcaccacc attctgggag ggctgtaccc atccaagtcc      60
atcctcctgt caggcactgt cctgcccagt gctcagaggt tccacatcaa cctgtgctct    120
gggaaccaca tcgccttcca cctgaacccc cgttttgatg agaatgctgt ggtccgcaac    180
acccagatcg acaactcctg ggggtctgag gagcgaagtc tgccccgaaa aatgcccttc    240
gtccgtggcc agagcttctc agtgtggatc ttgtgtgaag ctcactgcct caaggtggcc    300
gtggatggtc agcacctgtt tgaatactac catcgcctga ggaacctgcc caccatcaac    360
agactggaag tgggggcga catccagctg acccatgtgc agacatag                  408
```

<210> SEQ ID NO 72
<211> LENGTH: 408
<212> TYPE: DNA
<213> ORGANISM: Artificial Sequence
<220> FEATURE:
<223> OTHER INFORMATION: artificially synthesized sequence

<400> SEQUENCE: 72

```
gcccccctatc cgatgccttt catcaccacc attctgggag ggctgtaccc atccaagtcc    60
atcctcctgt caggcactgt cctgcccagt gctcagaggt tccacatcaa cctgtgctct   120
gggaaccaca tcgccttcca cctgaacccc cgttttgatg agaatgctgt ggtccgcaac   180
acccagatcg acaactcctg ggggtctgag gagcgaagtc tgccccgaaa aatgcccttc   240
gtccgtggcc agagcttctc agtgtggatc ttgtgtgaag ctcactgcct caaggtggcc   300
gtggatggtc agcacctgtt tgaatactac catcgcctga ggaacctgcc caccatcaac   360
agactggaag tgggggcga catccagctg acccatgtgc agacatag                 408
```

<210> SEQ ID NO 73
<211> LENGTH: 408
<212> TYPE: DNA
<213> ORGANISM: Artificial Sequence
<220> FEATURE:
<223> OTHER INFORMATION: artificially synthesized sequence

<400> SEQUENCE: 73

```
ccccccctatc cgatgccttt catcaccacc attctgggag ggctgtaccc atccaagtcc    60
atcctcctgt caggcactgt cctgcccagt gctcagaggt tccacatcaa cctgtgctct   120
gggaaccaca tcgccttcca cctgaacccc cgttttgatg agaatgctgt ggtccgcaac   180
acccagatcg acaactcctg ggggtctgag gagcgaagtc tgccccgaaa aatgcccttc   240
gtccgtggcc agagcttctc agtgtggatc ttgtgtgaag ctcactgcct caaggtggcc   300
gtggatggtc agcacctgtt tgaatactac catcgcctga ggaacctgcc caccatcaac   360
agactggaag tgggggcga catccagctg acccatgtgc agacatag                 408
```

<210> SEQ ID NO 74
<211> LENGTH: 405
<212> TYPE: DNA
<213> ORGANISM: Artificial Sequence
<220> FEATURE:
<223> OTHER INFORMATION: artificially synthesized sequence

<400> SEQUENCE: 74

```
gcctatccga tgcctttcat caccaccatt ctgggagggc tgtacccatc caagtccatc    60
ctcctgtcag gcactgtcct gcccagtgct cagaggttcc acatcaacct gtgctctggg   120
aaccacatcg ccttccacct gaaccccgt tttgatgaga atgctgtggt ccgcaacacc    180
```

```
cagatcgaca actcctgggg gtctgaggag cgaagtctgc ccgaaaaat gcccttcgtc    240 cgtggccaga gcttctcagt gtggatcttg tgtgaagctc actgcctcaa ggtggccgtg    300
gatggtcagc acctgtttga atactaccat cgcctgagga acctgcccac catcaacaga    360
ctggaagtgg ggggcgacat ccagctgacc catgtgcaga catag                    405
```

<210> SEQ ID NO 75
<211> LENGTH: 402
<212> TYPE: DNA
<213> ORGANISM: Artificial Sequence
<220> FEATURE:
<223> OTHER INFORMATION: artificially synthesized sequence

<400> SEQUENCE: 75

```
tatccgatgc ctttcatcac caccattctg ggagggctgt acccatccaa gtccatcctc     60
ctgtcaggca ctgtcctgcc cagtgctcag aggttccaca tcaacctgtg ctctgggaac    120
cacatcgcct tccacctgaa cccccgtttt gatgagaatg ctgtggtccg caacacccag    180
atcgacaact cctggggtc tgaggagcga agtctgcccc gaaaaatgcc cttcgtccgt    240
ggccagagct tctcagtgtg gatcttgtgt gaagctcact gcctcaaggt ggccgtggat    300
ggtcagcacc tgtttgaata ctaccatcgc ctgaggaacc tgcccaccat caacagactg    360
gaagtggggg gcgacatcca gctgacccat gtgcagacat ag                       402
```

<210> SEQ ID NO 76
<211> LENGTH: 399
<212> TYPE: DNA
<213> ORGANISM: Artificial Sequence
<220> FEATURE:
<223> OTHER INFORMATION: artificially synthesized sequence

<400> SEQUENCE: 76

```
ccgatgcctt tcatcaccac cattctggga gggctgtacc catccaagtc catcctcctg     60
tcaggcactg tcctgcccag tgctcagagg ttccacatca acctgtgctc tgggaaccac    120
atcgccttcc acctgaaccc cgttttgat gagaatgctg tggtccgcaa cacccagatc    180
gacaactcct ggggtctga ggagcgaagt ctgccccgaa aaatgccctt cgtccgtggc    240
cagagcttct cagtgtggat cttgtgtgaa gctcactgcc tcaaggtggc cgtggatggt    300
cagcacctgt ttgaatacta ccatcgcctg aggaacctgc ccaccatcaa cagactggaa    360
gtggggggcg acatccagct gacccatgtg cagacatag                           399
```

<210> SEQ ID NO 77
<211> LENGTH: 861
<212> TYPE: DNA
<213> ORGANISM: Artificial Sequence
<220> FEATURE:
<223> OTHER INFORMATION: artificially synthesized sequence

<400> SEQUENCE: 77

```
atggccttca gcggttccca ggctccctac ctgagtccag ctgtcccctt ttctgggact     60
attcaaggag gtctccagga cggacttcag atcactgtca atgggaccgt tctcagctcc    120
agtggaacca ggtttgctgt gaactttcag actggcttca gtggaaatga cattgccttc    180
cacttcaacc ctcggtttga agatggaggg tacgtggtgt gcaacacgag gcagaacgga    240
agctgggggc cgaggagag gaagacacac atgcctttcc agaaggggat gcctttgac    300 ctctgcttcc tggtgcagag ctcagatttc aaggtgatgg tgaacggtat cctcttcgtg    360
cagtacttcc accgcgtgcc cttccaccgt gtggacacca tctccgtcaa tggctctgtg    420
```

| | |
|---|---|
| cagctgtcct acatcagctt ccagtacccc cacccegcct atccgatgcc tttcatcacc | 480 |
| accattctgg gagggctgta cccatccaag tccatcctcc tgtcaggcac tgtcctgccc | 540 |
| agtgctcaga ggttccacat caacctgtgc tctgggaacc acatcgcctt ccacctgaac | 600 |
| ccccgttttg atgagaatgc tgtggtccgc aacacccaga tcgacaactc ctgggggtct | 660 |
| gaggagcgaa gtctgccccg aaaaatgccc ttcgtccgtg gccagagctt ctcagtgtgg | 720 |
| atcttgtgtg aagctcactg cctcaaggtg gccgtggatg gtcagcacct gtttgaatac | 780 |
| taccatcgcc tgaggaacct gcccaccatc aacagactgg aagtggggg cgacatccag | 840 |
| ctgacccatg tgcagacata g | 861 |

<210> SEQ ID NO 78
<211> LENGTH: 858
<212> TYPE: DNA
<213> ORGANISM: Artificial Sequence
<220> FEATURE:
<223> OTHER INFORMATION: artificially synthesized sequence

<400> SEQUENCE: 78

| | |
|---|---|
| atggccttca gcggttccca ggctccctac ctgagtccag ctgtccccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctgggggc ccgaggagag gaagacacac atgcctttcc agaagggat gcccttttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |
| cagctgtcct acatcagctt ccagcccac cccgcctatc cgatgccttt catcaccacc | 480 |
| attctgggag gctgtaccc atccaagtcc atcctcctgt caggcactgt cctgcccagt | 540 |
| gctcagaggt tccacatcaa cctgtgctct gggaaccaca tcgccttcca cctgaacccc | 600 |
| cgttttgatg agaatgctgt ggtccgcaac acccagatcg acaactcctg ggggtctgag | 660 |
| gagcgaagtc tgccccgaaa aatgcccttc gtccgtggcc agagcttctc agtgtggatc | 720 |
| ttgtgtgaag ctcactgcct caaggtggcc gtggatggtc agcacctgtt tgaatactac | 780 |
| catcgcctga ggaacctgcc caccatcaac agactggaag tgggggggcga catccagctg | 840 |
| acccatgtgc agacatag | 858 |

<210> SEQ ID NO 79
<211> LENGTH: 858
<212> TYPE: DNA
<213> ORGANISM: Artificial Sequence
<220> FEATURE:
<223> OTHER INFORMATION: artificially synthesized sequence

<400> SEQUENCE: 79

| | |
|---|---|
| atggccttca gcggttccca ggctccctac ctgagtccag ctgtccccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctgggggc ccgaggagag gaagacacac atgcctttcc agaagggat gcccttttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |

| | |
|---|---|
| cagctgtcct acatcagctt ccagcacccg cccgcctatc cgatgccttt catcaccacc | 480 |
| attctgggag ggctgtaccc atccaagtcc atcctcctgt caggcactgt cctgcccagt | 540 |
| gctcagaggt tccacatcaa cctgtgctct gggaaccaca tcgccttcca cctgaacccc | 600 |
| cgttttgatg agaatgctgt ggtccgcaac acccagatcg acaactcctg ggggtctgag | 660 |
| gagcgaagtc tgccccgaaa aatgcccttc gtccgtggcc agagcttctc agtgtggatc | 720 |
| ttgtgtgaag ctcactgcct caaggtggcc gtggatggtc agcacctgtt tgaatactac | 780 |
| catcgcctga ggaacctgcc caccatcaac agactggaag tggggggcga catccagctg | 840 |
| acccatgtgc agacatag | 858 |

<210> SEQ ID NO 80
<211> LENGTH: 855
<212> TYPE: DNA
<213> ORGANISM: Artificial Sequence
<220> FEATURE:
<223> OTHER INFORMATION: artificially synthesized sequence

<400> SEQUENCE: 80

| | |
|---|---|
| atggccttca gcggttccca ggctccctac ctgagtccag ctgtcccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctggggc ccgaggagag gaagacacac atgcctttcc agaaggggat gcctttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |
| cagctgtcct acatcagctt ccagcacccc gcctatccga tgcctttcat caccaccatt | 480 |
| ctgggagggc tgtacccatc caagtccatc ctcctgtcag gcactgtcct gcccagtgct | 540 |
| cagaggttcc acatcaacct gtgctctggg aaccacatcg ccttccacct gaaccccgt | 600 |
| tttgatgaga atgctgtggt ccgcaacacc cagatcgaca actcctgggg gtctgaggag | 660 |
| cgaagtctgc cccgaaaaat gcccttcgtc cgtggccaga gcttctcagt gtggatcttg | 720 |
| tgtgaagctc actgcctcaa ggtggccgtg gatggtcagc acctgtttga atactaccat | 780 |
| cgcctgagga acctgcccac catcaacaga ctggaagtgg gggcgacat ccagctgacc | 840 |
| catgtgcaga catag | 855 |

<210> SEQ ID NO 81
<211> LENGTH: 855
<212> TYPE: DNA
<213> ORGANISM: Artificial Sequence
<220> FEATURE:
<223> OTHER INFORMATION: artificially synthesized sequence

<400> SEQUENCE: 81

| | |
|---|---|
| atggccttca gcggttccca ggctccctac ctgagtccag ctgtcccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctggggc ccgaggagag gaagacacac atgcctttcc agaaggggat gcctttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |

| | |
|---|---|
| cagctgtcct acatcagctt ccagcacgcc gcctatccga tgcctttcat caccaccatt | 480 |
| ctgggagggc tgtacccatc caagtccatc ctcctgtcag gcactgtcct gcccagtgct | 540 |
| cagaggttcc acatcaacct gtgctctggg aaccacatcg ccttccacct gaaccccgt | 600 |
| tttgatgaga atgctgtggt ccgcaacacc cagatcgaca actcctgggg gtctgaggag | 660 |
| cgaagtctgc cccgaaaaat gcccttcgtc cgtggccaga gcttctcagt gtggatcttg | 720 |
| tgtgaagctc actgcctcaa ggtggccgtg gatggtcagc acctgtttga atactaccat | 780 |
| cgcctgagga acctgcccac catcaacaga ctggaagtgg ggggcgacat ccagctgacc | 840 |
| catgtgcaga catag | 855 |

<210> SEQ ID NO 82
<211> LENGTH: 855
<212> TYPE: DNA
<213> ORGANISM: Artificial Sequence
<220> FEATURE:
<223> OTHER INFORMATION: artificially synthesized sequence

<400> SEQUENCE: 82

| | |
|---|---|
| atggccttca gcggttccca ggctccctac ctgagtccag ctgtccccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctgggggc ccgaggagag gaagacacac atgcctttcc agaaggggat gcccttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |
| cagctgtcct acatcagctt ccagcacccc gcctatgcga tgcctttcat caccaccatt | 480 |
| ctgggagggc tgtacccatc caagtccatc ctcctgtcag gcactgtcct gcccagtgct | 540 |
| cagaggttcc acatcaacct gtgctctggg aaccacatcg ccttccacct gaaccccgt | 600 |
| tttgatgaga atgctgtggt ccgcaacacc cagatcgaca actcctgggg gtctgaggag | 660 |
| cgaagtctgc cccgaaaaat gcccttcgtc cgtggccaga gcttctcagt gtggatcttg | 720 |
| tgtgaagctc actgcctcaa ggtggccgtg gatggtcagc acctgtttga atactaccat | 780 |
| cgcctgagga acctgcccac catcaacaga ctggaagtgg ggggcgacat ccagctgacc | 840 |
| catgtgcaga catag | 855 |

<210> SEQ ID NO 83
<211> LENGTH: 855
<212> TYPE: DNA
<213> ORGANISM: Artificial Sequence
<220> FEATURE:
<223> OTHER INFORMATION: artificially synthesized sequence

<400> SEQUENCE: 83

| | |
|---|---|
| atggccttca gcggttccca ggctccctac ctgagtccag ctgtccccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctgggggc ccgaggagag gaagacacac atgcctttcc agaaggggat gcccttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |

| | |
|---|---|
| cagctgtcct acatcagctt ccagcacccc gccccgccga tgcctttcat caccaccatt | 480 |
| ctgggagggc tgtacccatc caagtccatc ctcctgtcag gcactgtcct gcccagtgct | 540 |
| cagaggttcc acatcaacct gtgctctggg aaccacatcg ccttccacct gaaccccgt | 600 |
| tttgatgaga atgctgtggt ccgcaacacc cagatcgaca actcctgggg gtctgaggag | 660 |
| cgaagtctgc cccgaaaaat gcccttcgtc cgtggccaga gcttctcagt gtggatcttg | 720 |
| tgtgaagctc actgcctcaa ggtggccgtg gatggtcagc acctgtttga atactaccat | 780 |
| cgcctgagga acctgcccac catcaacaga ctggaagtgg ggggcgacat ccagctgacc | 840 |
| catgtgcaga catag | 855 |

<210> SEQ ID NO 84
<211> LENGTH: 855
<212> TYPE: DNA
<213> ORGANISM: Artificial Sequence
<220> FEATURE:
<223> OTHER INFORMATION: artificially synthesized sequence

<400> SEQUENCE: 84

| | |
|---|---|
| atggccttca gcggttccca ggctccctac ctgagtccag ctgtcccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctgggggc ccgaggagag gaagacacac atgcctttcc agaaggggat gcccttttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |
| cagctgtcct acatcagctt ccagcacccc ccctatccga tgcctttcat caccaccatt | 480 |
| ctgggagggc tgtacccatc caagtccatc ctcctgtcag gcactgtcct gcccagtgct | 540 |
| cagaggttcc acatcaacct gtgctctggg aaccacatcg ccttccacct gaaccccgt | 600 |
| tttgatgaga atgctgtggt ccgcaacacc cagatcgaca actcctgggg gtctgaggag | 660 |
| cgaagtctgc cccgaaaaat gcccttcgtc cgtggccaga gcttctcagt gtggatcttg | 720 |
| tgtgaagctc actgcctcaa ggtggccgtg gatggtcagc acctgtttga atactaccat | 780 |
| cgcctgagga acctgcccac catcaacaga ctggaagtgg ggggcgacat ccagctgacc | 840 |
| catgtgcaga catag | 855 |

<210> SEQ ID NO 85
<211> LENGTH: 852
<212> TYPE: DNA
<213> ORGANISM: Artificial Sequence
<220> FEATURE:
<223> OTHER INFORMATION: artificially synthesized sequence

<400> SEQUENCE: 85

| | |
|---|---|
| atggccttca gcggttccca ggctccctac ctgagtccag ctgtcccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctgggggc ccgaggagag gaagacacac atgcctttcc agaaggggat gcccttttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |

| | |
|---|---|
| cagctgtcct acatcagctt ccagcccgcc tatccgatgc ctttcatcac caccattctg | 480 |
| ggagggctgt acccatccaa gtccatcctc ctgtcaggca ctgtcctgcc cagtgctcag | 540 |
| aggttccaca tcaacctgtg ctctgggaac cacatcgcct tccacctgaa ccccgtttt | 600 |
| gatgagaatg ctgtggtccg caacacccag atcgacaact cctggggtc tgaggagcga | 660 |
| agtctgcccc gaaaaatgcc cttcgtccgt ggccagagct tctcagtgtg atcttgtgt | 720 |
| gaagctcact gcctcaaggt ggccgtggat ggtcagcacc tgtttgaata ctaccatcgc | 780 |
| ctgaggaacc tgcccaccat caacagactg gaagtggggg gcgacatcca gctgacccat | 840 |
| gtgcagacat ag | 852 |

<210> SEQ ID NO 86
<211> LENGTH: 852
<212> TYPE: DNA
<213> ORGANISM: Artificial Sequence
<220> FEATURE:
<223> OTHER INFORMATION: artificially synthesized sequence

<400> SEQUENCE: 86

| | |
|---|---|
| atggccttca gcggttccca ggctccctac ctgagtccag ctgtcccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctgggggc ccgaggagag gaagacacac atgcctttcc agaagggggat gcccttttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |
| cagctgtcct acatcagctt ccaggccccc tatccgatgc ctttcatcac caccattctg | 480 |
| ggagggctgt acccatccaa gtccatcctc ctgtcaggca ctgtcctgcc cagtgctcag | 540 |
| aggttccaca tcaacctgtg ctctgggaac cacatcgcct tccacctgaa ccccgtttt | 600 |
| gatgagaatg ctgtggtccg caacacccag atcgacaact cctggggtc tgaggagcga | 660 |
| agtctgcccc gaaaaatgcc cttcgtccgt ggccagagct tctcagtgtg atcttgtgt | 720 |
| gaagctcact gcctcaaggt ggccgtggat ggtcagcacc tgtttgaata ctaccatcgc | 780 |
| ctgaggaacc tgcccaccat caacagactg gaagtggggg gcgacatcca gctgacccat | 840 |
| gtgcagacat ag | 852 |

<210> SEQ ID NO 87
<211> LENGTH: 852
<212> TYPE: DNA
<213> ORGANISM: Artificial Sequence
<220> FEATURE:
<223> OTHER INFORMATION: artificially synthesized sequence

<400> SEQUENCE: 87

| | |
|---|---|
| atggccttca gcggttccca ggctccctac ctgagtccag ctgtcccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctgggggc ccgaggagag gaagacacac atgcctttcc agaagggggat gcccttttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |

| | |
|---|---|
| cagctgtcct acatcagctt ccagccccc tatccgatgc ctttcatcac caccattctg | 480 |
| ggagggctgt acccatccaa gtccatcctc ctgtcaggca ctgtcctgcc cagtgctcag | 540 |
| aggttccaca tcaacctgtg ctctgggaac cacatcgcct tccacctgaa ccccgtttt | 600 |
| gatgagaatg ctgtggtccg caacacccag atcgacaact cctgggggtc tgaggagcga | 660 |
| agtctgcccc gaaaaatgcc cttcgtccgt ggccagagct tctcagtgtg atcttgtgt | 720 |
| gaagctcact gcctcaaggt ggccgtggat ggtcagcacc tgtttgaata ctaccatcgc | 780 |
| ctgaggaacc tgcccaccat caacagactg gaagtggggg gcgacatcca gctgacccat | 840 |
| gtgcagacat ag | 852 |

<210> SEQ ID NO 88
<211> LENGTH: 849
<212> TYPE: DNA
<213> ORGANISM: Artificial Sequence
<220> FEATURE:
<223> OTHER INFORMATION: artificially synthesized sequence

<400> SEQUENCE: 88

| | |
|---|---|
| atggccttca gcggttccca ggctccctac ctgagtccag ctgtcccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctggggc ccgaggagag gaagacacac atgcctttcc agaagggggat gccctttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |
| cagctgtcct acatcagctt ccaggcctat ccgatgcctt tcatcaccac cattctggga | 480 |
| gggctgtacc catccaagtc catcctcctg tcaggcactg tcctgcccag tgctcagagg | 540 |
| ttccacatca acctgtgctc tgggaaccac atcgccttcc acctgaaccc cgtttgat | 600 |
| gagaatgctg tggtccgcaa cacccagatc gacaactcct gggggtctga ggagcgaagt | 660 |
| ctgccccgaa aaatgccctt cgtccgtggc cagagcttct cagtggatc ttgtgtgaa | 720 |
| gctcactgcc tcaaggtggc cgtggatggt cagcacctgt ttgaatacta ccatcgcctg | 780 |
| aggaacctgc ccaccatcaa cagactggaa gtgggggcg acatccagct gacccatgtg | 840 |
| cagacatag | 849 |

<210> SEQ ID NO 89
<211> LENGTH: 846
<212> TYPE: DNA
<213> ORGANISM: Artificial Sequence
<220> FEATURE:
<223> OTHER INFORMATION: artificially synthesized sequence

<400> SEQUENCE: 89

| | |
|---|---|
| atggccttca gcggttccca ggctccctac ctgagtccag ctgtcccctt ttctgggact | 60 |
| attcaaggag gtctccagga cggacttcag atcactgtca atgggaccgt tctcagctcc | 120 |
| agtggaacca ggtttgctgt gaactttcag actggcttca gtggaaatga cattgccttc | 180 |
| cacttcaacc ctcggtttga agatggaggg tacgtggtgt gcaacacgag gcagaacgga | 240 |
| agctggggc ccgaggagag gaagacacac atgcctttcc agaagggggat gccctttgac | 300 |
| ctctgcttcc tggtgcagag ctcagatttc aaggtgatgg tgaacggtat cctcttcgtg | 360 |
| cagtacttcc accgcgtgcc cttccaccgt gtggacacca tctccgtcaa tggctctgtg | 420 |

```
cagctgtcct acatcagctt ccagtatccg atgcctttca tcaccaccat tctgggaggg    480
ctgtacccat ccaagtccat cctcctgtca ggcactgtcc tgcccagtgc tcagaggttc    540
cacatcaacc tgtgctctgg gaaccacatc gccttccacc tgaaccccg ttttgatgag     600 aatgctgtgg tccgcaacac ccagatcgac aactcctggg gtctgagga gcgaagtctg     660 ccccgaaaaa tgcccttcgt ccgtggccag agcttctcag tgtggatctt gtgtgaagct    720
cactgcctca aggtggccgt ggatggtcag cacctgtttg aatactacca tcgcctgagg    780
aacctgccca ccatcaacag actggaagtg gggggcgaca tccagctgac ccatgtgcag    840
acatag                                                              846
```

<210> SEQ ID NO 90
<211> LENGTH: 843
<212> TYPE: DNA
<213> ORGANISM: Artificial Sequence
<220> FEATURE:
<223> OTHER INFORMATION: artificially synthesized sequence

<400> SEQUENCE: 90

```
atggccttca gcggttccca ggctccctac ctgagtccag ctgtccccctt ttctgggact    60 attcaaggag gtctccagga cggacttcag atcactgtca atgggaccgt tctcagctcc   120
agtggaacca ggtttgctgt gaactttcag actggcttca gtggaaatga cattgccttc   180
cacttcaacc ctcggtttga agatggaggg tacgtggtgt gcaacacgag gcagaacgga   240
agctgggggc ccgaggagag gaagacacac atgcctttcc agaaggggat gccctttgac   300
ctctgcttcc tggtgcagag ctcagatttc aaggtgatgg tgaacggtat cctcttcgtg   360
cagtacttcc accgcgtgcc cttccaccgt gtggacacca tctccgtcaa tggctctgtg   420
cagctgtcct acatcagctt ccagccgatg cctttcatca ccaccattct gggagggctg   480
tacccatcca gtccatcct cctgtcaggc actgtcctgc ccagtgctca gaggttccac   540
atcaacctgt gctctgggaa ccacatcgcc ttccacctga ccccgtttt gatgagaat    600 gctgtggtcc gcaacaccca gatcgacaac tcctgggggt ctgaggagcg aagtctgccc   660
cgaaaaatgc ccttcgtccg tggccagagc ttctcagtgt ggatcttgtg tgaagctcac   720
tgcctcaagg tggccgtgga tggtcagcac ctgtttgaat actaccatcg cctgaggaac   780
ctgcccacca tcaacagact ggaagtgggg ggcgacatcc agctgaccca tgtgcagaca   840
tag                                                                843
```

<210> SEQ ID NO 91
<211> LENGTH: 296
<212> TYPE: PRT
<213> ORGANISM: Artificial Sequence
<220> FEATURE:
<223> OTHER INFORMATION: artificially synthesized sequence

<400> SEQUENCE: 91

```
Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60
```

```
Arg Phe Glu Asp Gly Gly Tyr Val Val Cys Asn Thr Arg Gln Asn Gly
 65                  70                  75                  80

Ser Trp Gly Pro Glu Glu Arg Lys Thr His Met Pro Phe Gln Lys Gly
                 85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln His Met Thr Pro Ala Ile Pro Pro Met Met Tyr Pro
145                 150                 155                 160

His Pro Ala Tyr Pro Met Pro Phe Ile Thr Thr Ile Leu Gly Gly Leu
                165                 170                 175

Tyr Pro Ser Lys Ser Ile Leu Leu Ser Gly Thr Val Leu Pro Ser Ala
            180                 185                 190

Gln Arg Phe His Ile Asn Leu Cys Ser Gly Asn His Ile Ala Phe His
        195                 200                 205

Leu Asn Pro Arg Phe Asp Glu Asn Ala Val Val Arg Asn Thr Gln Ile
210                 215                 220

Asp Asn Ser Trp Gly Ser Glu Arg Ser Leu Pro Arg Lys Met Pro
225                 230                 235                 240

Phe Val Arg Gly Gln Ser Phe Ser Val Trp Ile Leu Cys Glu Ala His
                245                 250                 255

Cys Leu Lys Val Ala Val Asp Gly Gln His Leu Phe Glu Tyr Tyr His
            260                 265                 270

Arg Leu Arg Asn Leu Pro Thr Ile Asn Arg Leu Glu Val Gly Gly Asp
        275                 280                 285

Ile Gln Leu Thr His Val Gln Thr
290                 295

<210> SEQ ID NO 92
<211> LENGTH: 891
<212> TYPE: DNA
<213> ORGANISM: Artificial Sequence
<220> FEATURE:
<223> OTHER INFORMATION: artificially synthesized sequence

<400> SEQUENCE: 92
atggccttca gcggttccca ggctccctac ctgagtccag ctgtcccctt ttctgggact      60
attcaaggag gtctccagga cggacttcag atcactgtca atgggaccgt tctcagctcc     120
agtggaacca ggtttgctgt gaactttcag actggcttca gtggaaatga cattgccttc     180
cacttcaacc tcggtttgga agatggaggg tacgtggtgt gcaacacgag gcagaacgga     240 agctggggc cgaggagag aagacacac atgcctttcc agaagggat gccctttgac         300 ctctgcttcc tggtgcagag ctcagatttc aaggtgatgg tgaacggtat cctcttcgtg     360
cagtacttcc accgcgtgcc cttccaccgt gtggacacca tctccgtcaa tggctctgtg     420
cagctgtcct acatcagctt ccagcatatg actcccgcca tcccaccat gatgtaccc     480 caccccgcct atccgatgcc tttcatcacc accattctgg agggctgta cccatccaag     540 tccatcctcc tgtcaggcac tgtcctgccc agtgctcaga ggttccacat caacctgtgc     600
tctgggaacc acatcgcctt ccacctgaac cccgttttg atgagaatgc tgtggtccgc     660
aacacccaga tcgacaactc ctgggggtct gaggagcgaa gtctgccccg aaaaatgccc     720
```

```
ttcgtccgtg gccagagctt ctcagtgtgg atcttgtgtg aagctcactg cctcaaggtg    780
gccgtggatg gtcagcacct gtttgaatac taccatcgcc tgaggaacct gcccaccatc    840
aacagactgg aagtgggggg cgacatccag ctgacccatg tgcagacata g             891
```

```
<210> SEQ ID NO 93
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 93
cgtcctcgtc ctcatatggc cttcagcggt tcccaggct                            39

<210> SEQ ID NO 94
<211> LENGTH: 24
<212> TYPE: DNA
<213> ORGANISM: Artificial Sequence
<220> FEATURE:
<223> OTHER INFORMATION: artificially synthesized sequence

<400> SEQUENCE: 94
ctggaagctg atgtaggaca gctg                                            24

<210> SEQ ID NO 95
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 95
tacatcagct tccagccacc tatgatgtac ccccacccc                            39

<210> SEQ ID NO 96
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 96
tacatcagct tccagatgat gtaccccac cccgcctat                             39

<210> SEQ ID NO 97
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 97
tacatcagct tccagtaccc ccaccccgcc tatccgatg                            39

<210> SEQ ID NO 98
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 98
tacatcagct tccagcccca ccccgcctat ccgatgcct                            39
```

```
<210> SEQ ID NO 99
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 99
tacatcagct tccagcaccc cgcctatccg atgcctttc                              39

<210> SEQ ID NO 100
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 100
tacatcagct tccagcccgc ctatccgatg cctttcatc                              39

<210> SEQ ID NO 101
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 101
tacatcagct tccaggccta tccgatgcct ttcatcacc                              39

<210> SEQ ID NO 102
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 102
tacatcagct tccagtatcc gatgcctttc atcaccacc                              39

<210> SEQ ID NO 103
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 103
tacatcagct tccagccgat gcctttcatc accaccatt                              39

<210> SEQ ID NO 104
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 104
tacatcagct tccagccttt catcaccacc attctggga                              39

<210> SEQ ID NO 105
<211> LENGTH: 36
<212> TYPE: DNA
<213> ORGANISM: Artificial Sequence
<220> FEATURE:
<223> OTHER INFORMATION: artificially synthesized sequence
```

```
<400> SEQUENCE: 105
cgaccgggat ccctatgtct gcacatgggt cagctg                              36

<210> SEQ ID NO 106
<211> LENGTH: 33
<212> TYPE: DNA
<213> ORGANISM: Artificial Sequence
<220> FEATURE:
<223> OTHER INFORMATION: artificially synthesized sequence

<400> SEQUENCE: 106
ataggcgggc gggtgctgga agctgatgta gga                                 33

<210> SEQ ID NO 107
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 107
gataggcggc gtgctggaag ctgatgta                                       28

<210> SEQ ID NO 108
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 108
aaggcatcgc ataggcgggg tgctggaa                                       28

<210> SEQ ID NO 109
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 109
tgatgaaagc catcggatag gcggggtg                                       28

<210> SEQ ID NO 110
<211> LENGTH: 41
<212> TYPE: DNA
<213> ORGANISM: Artificial Sequence
<220> FEATURE:
<223> OTHER INFORMATION: artificially synthesized sequence

<400> SEQUENCE: 110
tgatgaaagc catcgcatag gcggcgtgct ggaagctgat g                        41

<210> SEQ ID NO 111
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 111
tgaaaggcgg cggatagggg gggtgctg                                       28
```

<210> SEQ ID NO 112
<211> LENGTH: 29
<212> TYPE: DNA
<213> ORGANISM: Artificial Sequence
<220> FEATURE:
<223> OTHER INFORMATION: artificially synthesized sequence

<400> SEQUENCE: 112
ggcatcggcg gggcggggtg ctggaagct                                              29

<210> SEQ ID NO 113
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 113
tcggataggg ggggtgctgg aagctgat                                               28

<210> SEQ ID NO 114
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 114
cggatagggg gcctggaagc tgatgtagga                                             30

<210> SEQ ID NO 115
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 115
tcggataggg gggctggaag ctgatgta                                               28

<210> SEQ ID NO 116
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 116
tggtgatgaa agccatcgca taggcctgga agctgat                                     37

<210> SEQ ID NO 117
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 117
aggcatcgga ggggcctgga agctgatgta                                             30

<210> SEQ ID NO 118
<211> LENGTH: 33
<212> TYPE: DNA
<213> ORGANISM: Artificial Sequence
<220> FEATURE:
<223> OTHER INFORMATION: artificially synthesized sequence

```
<400> SEQUENCE: 118
agcttccagc acccgcccgc ctatccgatg cct                           33

<210> SEQ ID NO 119
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 119
ttccagcacg ccgcctatcc gatgcctt                                 28

<210> SEQ ID NO 120
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 120
cccgcctatg cgatgccttt catcacca                                 28

<210> SEQ ID NO 121
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 121
tatccgatgg ctttcatcac caccattc                                 28

<210> SEQ ID NO 122
<211> LENGTH: 43
<212> TYPE: DNA
<213> ORGANISM: Artificial Sequence
<220> FEATURE:
<223> OTHER INFORMATION: artificially synthesized sequence

<400> SEQUENCE: 122
ttccagcacg ccgcctatgc gatggctttc atcaccacca ttc                43

<210> SEQ ID NO 123
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 123
ctatccgccg cctttcatca ccaccatt                                 28

<210> SEQ ID NO 124
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 124
ccccgccccg ccgatgcctt tcatcacc                                 28
```

```
<210> SEQ ID NO 125
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 125
cagcaccccc cctatccgat gcctttca                                       28

<210> SEQ ID NO 126
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 126
ttccaggccc cctatccgat gcctttca                                       28

<210> SEQ ID NO 127
<211> LENGTH: 28
<212> TYPE: DNA
<213> ORGANISM: Artificial Sequence
<220> FEATURE:
<223> OTHER INFORMATION: artificially synthesized sequence

<400> SEQUENCE: 127
ccagcccccc tatccgatgc ctttcatc                                       28

<210> SEQ ID NO 128
<211> LENGTH: 37
<212> TYPE: DNA
<213> ORGANISM: Artificial Sequence
<220> FEATURE:
<223> OTHER INFORMATION: artificially synthesized sequence

<400> SEQUENCE: 128
ttccaggcct atgcgatggc tttcatcacc accattc                             37

<210> SEQ ID NO 129
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 129
ttccaggccc ctccgatgcc tttcatcacc                                     30

<210> SEQ ID NO 130
<211> LENGTH: 12
<212> TYPE: DNA
<213> ORGANISM: Artificial Sequence
<220> FEATURE:
<223> OTHER INFORMATION: artificially synthesized sequence

<400> SEQUENCE: 130 ccccacccg cc                                                         12

<210> SEQ ID NO 131
<211> LENGTH: 311
<212> TYPE: PRT
<213> ORGANISM: Homo sapiens
```

<400> SEQUENCE: 131

```
Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Gly Thr Arg Phe Ala Val Asn
            35                  40                  45

Phe Gln Thr Gly Phe Ser Gly Asn Asp Ile Ala Phe His Phe Asn Pro
        50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
130                 135                 140

Ile Ser Phe Gln Thr Gln Thr Val Ile His Thr Val Gln Ser Ala Pro
145                 150                 155                 160

Gly Gln Met Phe Ser Thr Pro Ala Ile Pro Pro Met Met Tyr Pro His
                165                 170                 175

Pro Ala Tyr Pro Met Pro Phe Ile Thr Thr Ile Leu Gly Gly Leu Tyr
            180                 185                 190

Pro Ser Lys Ser Ile Leu Leu Ser Gly Thr Val Leu Pro Ser Ala Gln
        195                 200                 205

Arg Phe His Ile Asn Leu Cys Ser Gly Asn His Ile Ala Phe His Leu
210                 215                 220

Asn Pro Arg Phe Asp Glu Asn Ala Val Val Arg Asn Thr Gln Ile Asp
225                 230                 235                 240

Asn Ser Trp Gly Ser Glu Glu Arg Ser Leu Pro Arg Lys Met Pro Phe
                245                 250                 255

Val Arg Gly Gln Ser Phe Ser Val Trp Ile Leu Cys Glu Ala His Cys
            260                 265                 270

Leu Lys Val Ala Val Asp Gly Gln His Leu Phe Glu Tyr Tyr His Arg
        275                 280                 285

Leu Arg Asn Leu Pro Thr Ile Asn Arg Leu Glu Val Gly Gly Asp Ile
    290                 295                 300

Gln Leu Thr His Val Gln Thr
305                 310
```

<210> SEQ ID NO 132
<211> LENGTH: 4
<212> TYPE: PRT
<213> ORGANISM: Artificial Sequence
<220> FEATURE:
<223> OTHER INFORMATION: artificially synthesized sequence

<400> SEQUENCE: 132

```
Pro His Pro Ala
1
```